US010434214B2

(12) United States Patent
Yu et al.

(10) Patent No.: US 10,434,214 B2
(45) Date of Patent: *Oct. 8, 2019

(54) HYALURONIC ACID-COLLAGEN MATRICES FOR DERMAL FILLING AND VOLUMIZING APPLICATIONS

(71) Applicant: Allergan, Inc., Irvine, CA (US)

(72) Inventors: Xiaojie Yu, Orange, CA (US); Nicholas J. Manesis, Escondido, CA (US); Jacob Pollock, Honolulu, HI (US)

(73) Assignee: Allergan, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/727,916

(22) Filed: Oct. 9, 2017

(65) Prior Publication Data

US 2018/0028719 A1 Feb. 1, 2018

Related U.S. Application Data

(60) Continuation of application No. 15/609,967, filed on May 31, 2017, now Pat. No. 9,795,711, which is a continuation of application No. 14/962,897, filed on Dec. 8, 2015, now Pat. No. 9,821,086, which is a division of application No. 13/667,581, filed on Nov. 2, 2012, now abandoned, which is a continuation-in-part of application No. 13/605,565, filed on Sep. 6, 2012, now abandoned, which is a continuation-in-part of application No. 13/603,213, filed on Sep. 4, 2012, now abandoned.

(60) Provisional application No. 61/555,970, filed on Nov. 4, 2011, provisional application No. 61/531,533, filed on Sep. 6, 2011.

(51) Int. Cl.
| | | |
|---|---|---|
| *A61K 8/04* | (2006.01) | |
| *A61K 8/73* | (2006.01) | |
| *A61L 27/24* | (2006.01) | |
| *A61L 27/26* | (2006.01) | |
| *A61L 27/36* | (2006.01) | |
| *A61L 27/52* | (2006.01) | |
| *A61Q 19/08* | (2006.01) | |

(52) U.S. Cl.
CPC ............ *A61L 27/24* (2013.01); *A61K 8/042* (2013.01); *A61K 8/735* (2013.01); *A61L 27/26* (2013.01); *A61L 27/3695* (2013.01); *A61L 27/52* (2013.01); *A61Q 19/08* (2013.01); *A61K 2800/91* (2013.01); *A61L 2400/06* (2013.01); *A61L 2430/34* (2013.01)

(58) Field of Classification Search
CPC .. A61L 2400/06; A61L 2430/34; A61L 27/24; A61L 27/26; A61L 27/3695; A61L 27/52; A61K 2800/91; A61K 8/042; A61K 8/735; A61Q 19/08; C08L 5/08; C08L 89/06
See application file for complete search history.

(56) References Cited

U.S. PATENT DOCUMENTS

| | | |
|---|---|---|
| 2,128,827 A | 8/1938 | Killian |
| 3,548,056 A | 12/1970 | Eigen et al. |
| 3,763,009 A | 10/1973 | Suzuki |
| 3,949,073 A | 4/1976 | Daniels et al. |
| 4,060,081 A | 11/1977 | Yannnas et al. |
| 4,140,537 A | 2/1979 | Luck et al. |
| 4,233,360 A | 11/1980 | Luck et al. |
| 4,273,705 A | 6/1981 | Kato |
| 4,279,812 A | 7/1981 | Cioca |
| 4,424,208 A | 1/1984 | Wallace et al. |
| 4,501,306 A | 2/1985 | Chu et al. |
| 4,582,640 A | 4/1986 | Smestad et al. |
| 4,582,865 A | 4/1986 | Balazs et al. |
| 4,605,691 A | 8/1986 | Balazs et al. |
| 4,636,524 A | 1/1987 | Balazs |
| 4,642,117 A | 2/1987 | Nguyen et al. |
| 4,657,553 A | 4/1987 | Taylor |
| 4,713,448 A | 12/1987 | Balazs |
| 4,716,154 A | 12/1987 | Malson et al. |
| 4,772,419 A | 9/1988 | Malson et al. |
| 4,803,075 A | 2/1989 | Wallace et al. |
| 4,886,787 A | 12/1989 | De Belder et al. |
| 4,896,787 A | 1/1990 | Delamour et al. |
| 5,009,013 A | 4/1991 | Wiklund |
| 5,087,446 A | 2/1992 | Suzuki et al. |
| 5,091,171 A | 2/1992 | Yu et al. |
| 5,143,724 A | 9/1992 | Leshchiner et al. |
| 5,246,698 A | 9/1993 | Leshchiner et al. |
| 5,314,874 A | 5/1994 | Miyata et al. |
| 5,328,955 A | 7/1994 | Rhee et al. |

(Continued)

FOREIGN PATENT DOCUMENTS

| | | |
|---|---|---|
| CA | 949965 | 6/1974 |
| CA | 2805008 | 1/2012 |

(Continued)

OTHER PUBLICATIONS

*Aesthetic Buyers Guide*, "Juvéderm Raises Standards" Jan./Feb. 2007 (5 pp.), www.miinews.com.
Adams, "An Analysis of Clinical Studies of the Uses of Crosslinked Hyaluronan, Hylan, in the Treatment of Osteoarthritis", J. Rheumatol Suppl., Aug. 1993; 39:16-8.
Albano, Emanuele, et al., "Hyroxyethyl Radicals in Ethanol Hepatotoxicity," Frontiers in Bioscience 4:533-540 (1999).
Allemann et al., "Hyaluronic acid gel (JUVADERM) preparations in the treatment of facial wrinkles and folds", 2008, Clinical Interventions in Aging, vol. 3, No. 4, pp. 629-634.

(Continued)

*Primary Examiner* — Karlheinz R. Skowronek
*Assistant Examiner* — Li N Komatsu
(74) *Attorney, Agent, or Firm* — Nathan S. Smith; Christopher J. Betti; Morgan, Lewis & Bockius LLP

(57) ABSTRACT

Hydrogels comprising a macromolecular matrix and water may be used for aesthetic fillers, for example, dermal fillers. The macromolecular matrix may include a crosslinked combination of hyaluronic acid and collagen.

18 Claims, 3 Drawing Sheets

(56) References Cited

U.S. PATENT DOCUMENTS

| | | |
|---|---|---|
| 5,356,883 A | 10/1994 | Kuo et al. |
| 5,399,351 A | 3/1995 | Leshchiner et al. |
| 5,428,024 A | 6/1995 | Chu et al. |
| 5,531,716 A | 7/1996 | Luzio et al. |
| 5,565,519 A | 10/1996 | Rhee et al. |
| 5,571,503 A | 11/1996 | Mausner |
| 5,614,587 A | 3/1997 | Rhee et al. |
| 5,616,568 A | 4/1997 | Pouyani et al. |
| 5,616,611 A | 4/1997 | Yamamoto |
| 5,616,689 A | 4/1997 | Shenoy et al. |
| 5,633,001 A | 5/1997 | Agerup |
| 5,643,464 A | 7/1997 | Rhee et al. |
| 5,676,964 A | 10/1997 | della Valle |
| 5,823,671 A | 10/1998 | Mitchell et al. |
| 5,824,333 A | 10/1998 | Scopelianos et al. |
| 5,827,529 A | 10/1998 | Ono et al. |
| 5,843,907 A | 12/1998 | Sakai |
| 5,880,107 A | 3/1999 | Buenter |
| 5,886,042 A | 3/1999 | Yu et al. |
| 5,935,164 A | 8/1999 | Iversen |
| 5,972,326 A | 10/1999 | Galin et al. |
| 5,972,385 A | 10/1999 | Liu et al. |
| 5,980,930 A | 11/1999 | Fenton et al. |
| 6,013,679 A | 1/2000 | Kuo et al. |
| 6,066,325 A | 5/2000 | Wallace et al. |
| 6,129,751 A | 10/2000 | Hubbell |
| 6,129,761 A | 10/2000 | Hubbell |
| 6,224,857 B1 | 5/2001 | Romeo et al. |
| 6,335,035 B1 | 1/2002 | Drizen et al. |
| 6,372,494 B1 | 4/2002 | Naughton et al. |
| 6,383,218 B1 | 5/2002 | Sourdille et al. |
| 6,383,219 B1 | 5/2002 | Telandro et al. |
| 6,418,934 B1 | 7/2002 | Chin |
| 6,495,148 B1 | 12/2002 | Abbiati |
| 6,521,223 B1 | 2/2003 | Calias et al. |
| 6,544,503 B1 | 4/2003 | Vanderhoff et al. |
| 6,627,620 B1 | 9/2003 | Nielsen |
| 6,630,486 B1 | 10/2003 | Royer |
| 6,685,963 B1 | 2/2004 | Taupin et al. |
| 6,716,251 B1 | 4/2004 | Asius et al. |
| 6,734,298 B1 | 5/2004 | Barbucci |
| 6,767,924 B2 | 7/2004 | Yu et al. |
| 6,767,928 B1 | 7/2004 | Murphy et al. |
| 6,852,255 B2 | 2/2005 | Yang |
| 6,893,466 B2 | 5/2005 | Trieu |
| 6,903,199 B2 | 6/2005 | Moon |
| 6,921,819 B2 | 7/2005 | Piron et al. |
| 6,924,273 B2 | 8/2005 | Pierce |
| 6,939,562 B2 | 9/2005 | Spiro et al. |
| 6,979,440 B2 | 12/2005 | Shefer et al. |
| 6,991,652 B2 | 1/2006 | Burg |
| 7,015,198 B1 | 3/2006 | Orentreich |
| 7,119,062 B1 | 10/2006 | Alvis et al. |
| 7,129,209 B2 | 10/2006 | Rhee |
| 7,166,570 B2 | 1/2007 | Hunter et al. |
| 7,192,984 B2 | 3/2007 | Berg |
| 7,196,180 B2 | 3/2007 | Aeschlimann |
| 7,314,636 B2 | 1/2008 | Caseres et al. |
| 7,316,822 B2 | 1/2008 | Binette |
| 7,318,822 B2 | 1/2008 | Binette |
| 7,491,709 B2 | 2/2009 | Carey |
| 7,741,476 B2 | 6/2010 | Lebreton |
| 7,767,452 B2 | 8/2010 | Kleinsek |
| 7,799,767 B2 | 9/2010 | Lamberti et al. |
| 7,875,296 B2 | 1/2011 | Binette |
| 7,902,171 B2 | 3/2011 | Reinmuller et al. |
| 8,052,990 B2 | 11/2011 | Hermitte et al. |
| 8,053,423 B2 | 11/2011 | Lamberti et al. |
| 8,124,120 B2 | 2/2012 | Sadozai |
| 8,137,702 B2 | 3/2012 | Binette et al. |
| 8,153,591 B2 | 4/2012 | Masters et al. |
| 8,246,947 B2 | 8/2012 | Hedrick et al. |
| 8,288,347 B2 | 10/2012 | Collette et al. |
| 8,318,695 B2 | 11/2012 | Stroumpoulis et al. |
| 8,338,375 B2 | 12/2012 | Schroeder et al. |
| 8,338,388 B2 | 12/2012 | Lebreton |
| 8,357,795 B2 | 1/2013 | Lebreton |
| 8,394,782 B2 | 3/2013 | Strompoulis |
| 8,394,783 B2 | 3/2013 | Strompoulis |
| 8,394,784 B2 | 3/2013 | Stroumpoulis et al. |
| 8,455,465 B2 | 6/2013 | Molliard |
| 8,512,752 B2 | 8/2013 | Crescenzi et al. |
| 8,513,216 B2 | 8/2013 | Strompoulis |
| 8,524,213 B2 | 9/2013 | Leshchine |
| 8,563,532 B2 | 10/2013 | Lebreton |
| 8,575,129 B2 | 11/2013 | Bellini |
| 8,586,562 B2 | 11/2013 | Lebreton |
| 8,691,279 B2 | 4/2014 | Guillen |
| 8,853,184 B2 | 10/2014 | Strompoulis |
| 9,662,422 B2 | 5/2017 | Pollock et al. |
| 2001/0039336 A1 | 11/2001 | Miller et al. |
| 2002/0102311 A1 | 8/2002 | Gustavsson et al. |
| 2002/0160109 A1 | 10/2002 | Yeo et al. |
| 2003/0031638 A1 | 2/2003 | Joshi et al. |
| 2003/0093157 A1 | 5/2003 | Casares et al. |
| 2003/0119985 A1 | 6/2003 | Sehl et al. |
| 2003/0148995 A1 | 8/2003 | Piron et al. |
| 2004/0032056 A1 | 2/2004 | Vang et al. |
| 2004/0101959 A1 | 5/2004 | Marko et al. |
| 2004/0127698 A1 | 7/2004 | Tsai et al. |
| 2004/0127699 A1 | 7/2004 | Zhao et al. |
| 2004/0199241 A1 | 10/2004 | Gravett et al. |
| 2004/0265389 A1 | 12/2004 | Yui et al. |
| 2005/0013729 A1 | 1/2005 | Brown-Skrobot |
| 2005/0025755 A1 | 2/2005 | Hedrick et al. |
| 2005/0101582 A1 | 5/2005 | Lyons et al. |
| 2005/0136122 A1 | 6/2005 | Sadozai et al. |
| 2005/0142152 A1 | 6/2005 | Leshchiner et al. |
| 2005/0181007 A1 | 8/2005 | Hunter |
| 2005/0186261 A1 | 8/2005 | Avelar |
| 2005/0186673 A1 | 8/2005 | Geistlich et al. |
| 2005/0227936 A1 | 10/2005 | Agerup |
| 2005/0271729 A1 | 12/2005 | Wang |
| 2005/0281880 A1 | 12/2005 | Wang |
| 2005/0287180 A1 | 12/2005 | Chen |
| 2006/0029578 A1 | 2/2006 | Hoemann et al. |
| 2006/0040894 A1 | 2/2006 | Hunter et al. |
| 2006/0095137 A1 | 5/2006 | Chung et al. |
| 2006/0105022 A1 | 5/2006 | Yokokawa et al. |
| 2006/0122147 A1 | 6/2006 | Wohlrab |
| 2006/0141049 A1 | 6/2006 | Lyons et al. |
| 2006/0147483 A1 | 7/2006 | Chaouk et al. |
| 2006/0189516 A1 | 8/2006 | Yang |
| 2006/0194758 A1 | 8/2006 | Lebreton |
| 2006/0246137 A1 | 11/2006 | Hermitte et al. |
| 2006/0257488 A1 | 11/2006 | Hubbard |
| 2006/0286769 A1 | 12/2006 | Tsuchiya et al. |
| 2007/0003525 A1 | 1/2007 | Moehlenbruck |
| 2007/0026070 A1 | 2/2007 | Vonwiller et al. |
| 2007/0036745 A1 | 2/2007 | Leshchiner et al. |
| 2007/0066816 A1 | 3/2007 | Tsai et al. |
| 2007/0077292 A1 | 4/2007 | Pinsky |
| 2007/0104692 A1 | 5/2007 | Quijano et al. |
| 2007/0104893 A9 | 5/2007 | Quijano et al. |
| 2007/0203095 A1 | 8/2007 | Sadozai et al. |
| 2007/0212385 A1 | 9/2007 | David |
| 2007/0224247 A1 | 9/2007 | Chudzik |
| 2007/0224278 A1 | 9/2007 | Lyons et al. |
| 2007/0298005 A1 | 12/2007 | Thibault |
| 2008/0028578 A1 | 2/2008 | Hoemann et al. |
| 2008/0044476 A1 | 2/2008 | Lyons et al. |
| 2008/0057091 A1 | 3/2008 | Abdellaoul |
| 2008/0089918 A1 | 4/2008 | Lebreton |
| 2008/0188416 A1 | 8/2008 | Bernstein |
| 2008/0193538 A1 | 8/2008 | Kitazono et al. |
| 2008/0200430 A1 | 8/2008 | Biterman et al. |
| 2008/0207794 A1 | 8/2008 | Wright et al. |
| 2008/0241252 A1 | 10/2008 | Lyons |
| 2008/0268051 A1 | 10/2008 | Lyons |
| 2008/0274946 A1 | 11/2008 | Gimpapa |
| 2008/0279806 A1 | 11/2008 | Cho |
| 2008/0293637 A1 | 11/2008 | Schroeder et al. |
| 2008/0300681 A1 | 12/2008 | Rigotti et al. |
| 2009/0017091 A1 | 1/2009 | Daniloff et al. |

(56) References Cited

U.S. PATENT DOCUMENTS

| | | |
|---|---|---|
| 2009/0018102 A1 | 1/2009 | Moutet |
| 2009/0022808 A1 | 1/2009 | Champion |
| 2009/0028817 A1 | 1/2009 | Niklason et al. |
| 2009/0036403 A1 | 2/2009 | Stroumpoulis et al. |
| 2009/0042834 A1 | 2/2009 | Karageozian et al. |
| 2009/0093755 A1 | 4/2009 | Schroeder et al. |
| 2009/0098177 A1 | 4/2009 | Werkmeister et al. |
| 2009/0110671 A1 | 4/2009 | Miyata et al. |
| 2009/0110736 A1 | 4/2009 | Boutros |
| 2009/0123547 A1 | 5/2009 | Hill et al. |
| 2009/0124552 A1 | 5/2009 | Hill et al. |
| 2009/0143331 A1 | 6/2009 | Stroumpoulis et al. |
| 2009/0143348 A1 | 6/2009 | Tezel et al. |
| 2009/0148527 A1 | 6/2009 | Robinson |
| 2009/0155314 A1 | 6/2009 | Tezel |
| 2009/0155362 A1 | 6/2009 | Longin |
| 2009/0162415 A1 | 6/2009 | Huang et al. |
| 2009/0169615 A1 | 7/2009 | Pinsky |
| 2009/0181104 A1 | 7/2009 | Rigotti et al. |
| 2009/0263447 A1 | 10/2009 | Asius et al. |
| 2009/0291986 A1 | 11/2009 | Pappas et al. |
| 2009/0297632 A1 | 12/2009 | Waugh |
| 2009/0317376 A1 | 12/2009 | Zukowska et al. |
| 2010/0004198 A1 | 1/2010 | Stroumpoulis et al. |
| 2010/0028437 A1 | 2/2010 | Lebreton |
| 2010/0035838 A1 | 2/2010 | Herber et al. |
| 2010/0041788 A1 | 2/2010 | Voigts et al. |
| 2010/0098764 A1 | 4/2010 | Stroumpoulis et al. |
| 2010/0098794 A1 | 4/2010 | Armand |
| 2010/0099623 A1 | 4/2010 | Schroeder et al. |
| 2010/0111919 A1 | 5/2010 | Abuzaina et al. |
| 2010/0136070 A1 | 6/2010 | Dobak et al. |
| 2010/0160948 A1 | 6/2010 | Rigotti et al. |
| 2010/0161052 A1 | 6/2010 | Rigotti et al. |
| 2010/0168780 A1 | 7/2010 | Rigotti et al. |
| 2010/0226988 A1 | 9/2010 | Lebreton |
| 2010/0247851 A1 | 9/2010 | Kastler |
| 2010/0249924 A1 | 9/2010 | Powell et al. |
| 2010/0255068 A1 | 10/2010 | Stroumpoulis et al. |
| 2010/0316683 A1 | 12/2010 | Piron |
| 2011/0008408 A1 | 1/2011 | Altman et al. |
| 2011/0008436 A1 | 1/2011 | Altman et al. |
| 2011/0008437 A1 | 1/2011 | Altman et al. |
| 2011/0014283 A1 | 1/2011 | Altman et al. |
| 2011/0014287 A1 | 1/2011 | Altman et al. |
| 2011/0020409 A1 | 1/2011 | Altman et al. |
| 2011/0034684 A1 | 2/2011 | Yokokawa |
| 2011/0052695 A1 | 3/2011 | Jiang et al. |
| 2011/0070281 A1 | 3/2011 | Altman |
| 2011/0077737 A1 | 3/2011 | Stroumpoulis et al. |
| 2011/0087381 A1 | 4/2011 | Binette |
| 2011/0097381 A1 | 4/2011 | Altman |
| 2011/0104800 A1 | 5/2011 | Kensy et al. |
| 2011/0111031 A1 | 5/2011 | Jiang et al. |
| 2011/0118206 A1 | 5/2011 | Lebreton |
| 2011/0150823 A1 | 6/2011 | Huang |
| 2011/0150846 A1 | 6/2011 | Van Epps |
| 2011/0171286 A1 | 7/2011 | Cecile et al. |
| 2011/0171310 A1 | 7/2011 | Gousse |
| 2011/0171311 A1 | 7/2011 | Gousse et al. |
| 2011/0172180 A1 | 7/2011 | Gousse et al. |
| 2011/0183001 A1 | 7/2011 | Rosson et al. |
| 2011/0183408 A1 | 7/2011 | Kensy |
| 2011/0189292 A1 | 8/2011 | Lebreton et al. |
| 2011/0194945 A1 | 8/2011 | Kensy et al. |
| 2011/0224164 A1 | 9/2011 | Lebreton |
| 2011/0229574 A1 | 9/2011 | Guillen et al. |
| 2011/0295238 A1 | 12/2011 | Kensy et al. |
| 2012/0010146 A1 | 1/2012 | Han et al. |
| 2012/0018959 A1 | 1/2012 | Andersson et al. |
| 2012/0034462 A1 | 2/2012 | Stroumpoulis et al. |
| 2012/0045420 A1 | 2/2012 | Van Epps et al. |
| 2012/0071437 A1 | 3/2012 | Stroumpoulis et al. |
| 2012/0076868 A1 | 3/2012 | Lamberti et al. |
| 2012/0095206 A1 | 4/2012 | Chen |
| 2012/0100217 A1 | 4/2012 | Green |
| 2012/0100611 A1 | 4/2012 | Kensy et al. |
| 2012/0156265 A1 | 6/2012 | Binette et al. |
| 2012/0164098 A1 | 6/2012 | Schroeder et al. |
| 2012/0164116 A1 | 6/2012 | Van Epps |
| 2012/0165838 A1 | 6/2012 | Van Epps |
| 2012/0171265 A1 | 7/2012 | Altman et al. |
| 2012/0172317 A1 | 7/2012 | Altman et al. |
| 2012/0172328 A1 | 7/2012 | Lebreton |
| 2012/0172985 A1 | 7/2012 | Altman et al. |
| 2012/0189589 A1 | 7/2012 | Van Epps et al. |
| 2012/0189590 A1 | 7/2012 | Van Epps et al. |
| 2012/0189699 A1 | 7/2012 | Stroumpoulis et al. |
| 2012/0189708 A1 | 7/2012 | Van Epps et al. |
| 2012/0190644 A1 | 7/2012 | D'esto |
| 2012/0207837 A1 | 8/2012 | Powell et al. |
| 2012/0208890 A1 | 8/2012 | Gousse et al. |
| 2012/0209381 A1 | 8/2012 | Powell et al. |
| 2012/0213852 A1 | 8/2012 | Van Epps et al. |
| 2012/0213853 A1 | 8/2012 | Van Epps et al. |
| 2012/0219627 A1 | 8/2012 | Van Epps et al. |
| 2012/0225842 A1 | 9/2012 | Cecile et al. |
| 2012/0232030 A1 | 9/2012 | Gousse et al. |
| 2012/0263686 A1 | 10/2012 | Van Epps et al. |
| 2012/0265297 A1 | 10/2012 | Altman et al. |
| 2012/0269777 A1 | 10/2012 | Van Epps et al. |
| 2012/0295870 A1 | 11/2012 | Lebreton |
| 2013/0023658 A1 | 1/2013 | Stroumpoulis et al. |
| 2013/0041038 A1 | 2/2013 | Lebreton |
| 2013/0041039 A1 | 2/2013 | Lebreton |
| 2013/0072453 A1 | 3/2013 | Gousse et al. |
| 2013/0096081 A1 | 4/2013 | Njikang |
| 2013/0116188 A1 | 5/2013 | Pollock et al. |
| 2013/0116190 A1 | 5/2013 | Pollock et al. |
| 2013/0116411 A1 | 5/2013 | Pollock et al. |
| 2013/0123210 A1 | 5/2013 | Liu |
| 2013/0129835 A1 | 5/2013 | Pollock et al. |
| 2013/0131011 A1 | 5/2013 | Lebreton |
| 2013/0131655 A1 | 5/2013 | Rigotti et al. |
| 2013/0136780 A1 | 5/2013 | Tezel et al. |
| 2013/0203696 A1 | 8/2013 | Liu |
| 2013/0203856 A1 | 8/2013 | Cho, II |
| 2013/0209532 A1 | 8/2013 | Stroumpoulis et al. |
| 2013/0210760 A1 | 8/2013 | Liu |
| 2013/0237615 A1 | 9/2013 | Meunier |
| 2013/0244943 A1 | 9/2013 | Yu et al. |
| 2013/0244970 A1 | 9/2013 | Lebreton |
| 2013/0274222 A1 | 10/2013 | Horne |
| 2013/0287758 A1 | 10/2013 | Tozzi |
| 2014/0011990 A1 | 1/2014 | Lebreton |
| 2014/0227235 A1 | 8/2014 | Kim et al. |
| 2016/0113855 A1 | 4/2016 | Njikang |
| 2017/0273886 A1 | 9/2017 | Gousse |

FOREIGN PATENT DOCUMENTS

| | | | |
|---|---|---|---|
| CN | 102548590 | 7/2012 | |
| EP | 0273823 | 7/1988 | |
| EP | 0416250 | 3/1991 | |
| EP | 0416846 | 3/1991 | |
| EP | 1247522 | 10/2002 | |
| EP | 1419792 | 4/2003 | |
| EP | 1398131 | 3/2004 | |
| EP | 1115433 | 12/2004 | |
| EP | 1532991 | 5/2005 | |
| EP | 1726299 | 11/2006 | |
| EP | 1932530 | 6/2008 | |
| EP | 2236523 | 10/2010 | |
| FR | 2733427 | 10/1996 | |
| FR | 2752843 | 3/1998 | |
| FR | 2920000 | 2/2009 | |
| FR | 2924615 | 6/2009 | |
| JP | 55-153711 | 11/1980 | |
| JP | 2002/080501 A | 3/2002 | ............ C08B 37/08 |
| JP | 2007-063177 | 3/2007 | |
| JP | 2002/080501 | 10/2013 | |
| KR | 20110138765 | 12/2011 | |
| KR | 20130018518 | 2/2013 | |
| WO | WO 1986/000079 | 1/1986 | |

(56) References Cited

FOREIGN PATENT DOCUMENTS

| | | |
|---|---|---|
| WO | WO 1986/000912 | 2/1986 |
| WO | WO 1992/000105 | 1/1992 |
| WO | WO 1992/020349 | 11/1992 |
| WO | WO 1994/001468 | 1/1994 |
| WO | WO 1994/002517 | 2/1994 |
| WO | WO 1996/033751 | 1/1996 |
| WO | WO 1997/004012 | 2/1997 |
| WO | WO 1998/035639 | 8/1998 |
| WO | WO 1998/035640 | 8/1998 |
| WO | WO 2000/001428 | 1/2000 |
| WO | WO 00/08061 | 2/2000 |
| WO | 200046252 A1 | 8/2000 |
| WO | WO 2001/079342 | 10/2001 |
| WO | WO 2002/005753 | 1/2002 |
| WO | WO 2002/006350 | 1/2002 |
| WO | WO 2002/009792 | 2/2002 |
| WO | WO 2002/017713 | 3/2002 |
| WO | WO 2003/007782 | 1/2003 |
| WO | WO 2004/020473 | 3/2004 |
| WO | WO 2004/022603 | 3/2004 |
| WO | WO 2004/067575 | 8/2004 |
| WO | WO 2004/073759 | 9/2004 |
| WO | WO 2004/092223 | 10/2004 |
| WO | WO 2005/040224 | 5/2005 |
| WO | WO 2005/067944 | 7/2005 |
| WO | 2005052035 A1 | 8/2005 |
| WO | WO 2005/074913 | 8/2005 |
| WO | WO 2005/112888 | 12/2005 |
| WO | WO 2006/021644 | 3/2006 |
| WO | WO 2006/023645 | 3/2006 |
| WO | WO 2006/048671 | 5/2006 |
| WO | WO 2006/056204 | 6/2006 |
| WO | WO 2006/067608 | 6/2006 |
| WO | WO 2007/018124 | 2/2007 |
| WO | WO 2007/070617 | 6/2007 |
| WO | WO 2007/077399 | 7/2007 |
| WO | WO 2007/128923 | 11/2007 |
| WO | WO 2007/136738 | 11/2007 |
| WO | 2008015490 A1 | 2/2008 |
| WO | WO 2008/015249 | 2/2008 |
| WO | WO 2008/034176 | 3/2008 |
| WO | 2008/063589 | 5/2008 |
| WO | WO 2008/068297 | 6/2008 |
| WO | WO 2008/072230 | 6/2008 |
| WO | WO 2008/077172 | 7/2008 |
| WO | WO 2008/098019 | 8/2008 |
| WO | WO 2008/139122 | 11/2008 |
| WO | 2008146071 | 12/2008 |
| WO | 2009003135 | 12/2008 |
| WO | WO 2008/148967 | 12/2008 |
| WO | WO 2008/157608 | 12/2008 |
| WO | 2009026158 A3 | 2/2009 |
| WO | WO 2009/024350 | 2/2009 |
| WO | WO 2009/024719 | 2/2009 |
| WO | WO 2009/026158 | 2/2009 |
| WO | WO 2009/028764 | 3/2009 |
| WO | WO 2009/034559 | 3/2009 |
| WO | WO 2009/073437 | 6/2009 |
| WO | WO 2010/003104 A2 | 1/2010 ............ A81L 27/18 |
| WO | WO 2010/003797 | 1/2010 |
| WO | WO 2010/015900 | 2/2010 |
| WO | 2010/026288 | 3/2010 |
| WO | WO 2010/027471 | 3/2010 |
| WO | WO 2010/028025 | 3/2010 |
| WO | WO 2010/029344 | 3/2010 |
| WO | WO 2010/038771 | 4/2010 |
| WO | WO 2010/051641 | 5/2010 |
| WO | WO 2010/052430 | 5/2010 |
| WO | WO 2010/053918 | 5/2010 |
| WO | WO 2010/061005 | 6/2010 |
| WO | WO 2011/023355 | 3/2011 |
| WO | WO 2011/072399 | 6/2011 |
| WO | WO 2011/119468 | 9/2011 |
| WO | WO 2011/135150 | 11/2011 |
| WO | WO 2012/008722 | 1/2012 |
| WO | 2012/077055 | 6/2012 |
| WO | 2013015579 A2 | 1/2013 |

OTHER PUBLICATIONS

Antunes, Alberto A., et al., "Efficacy of Intrarectal Lidocain Hydrochloride Gel for Pain control in Patients Undergoing Transrectal Prostate Biopsy", International Braz J Urol, vol. 30(5):380-383, Sep.-Oct. 2004.

Atanassoff, Peter G., et al., "The Effect of Intradermal Administration of Lidocaine and Morphine on the Response to Thermal Stimulation", Anesth Analg 1997; 84:1340-3.

Baumann et al. "JUVEDERM vs. ZYPLAST Nasolabial Fold Study Group, Comparison of smooth-gel hyaluronic acid dermal fillers with cross-linked bovine collagen: a multicenter, double-masked, randomized, within-subject study." Dermatol. Surg. 33(Suppl 2):S128-S135 (2007).

Beasley et al. :Hyaluronic acid fillers: a comprehensive review. Facial Plast. Surg. 25(2): 86-94 (2009).

Beer "Dermal fillers and combinations of fillers for facial rejuvenation." Dermatol. Clin. 27(4):427-432 (2009).

Belda, Jose I., et al., "Hyaluronic acid combined with mannitol to improve protection against free-radical endothelial damage: Experimental Model," J.Cataract Refract Surg 2005;31:1213-1218.

Bircher, Andreas J., et al., "Delayed-type hypersensitivity to subcutaneous lidocaine with tolerance to articaine: confirmation by in vivo and in vitro tests", Contact Dermatitis 1996, 34, 387-389.

Bluel et al., "Evaluations of Reconstituted Collagen Tape as a Model for Chemically Modified Soft Tissues", Biomat. Med. De. Art. Org., 9(1):37-46 (1981).

Buck et al, "Injectable Fillers for our Facial Rejuvenation: a Review", Journal of Plastic, Reconstructive and Aesthetic Surgery, (2009), 62:11-18, XP002668828.

Capozzi et al., "Distant Migration of Silicone Gel From a Ruptured Breats Implant", Plastic and Reconstructive Surgery, 1978; 62:302-3.

Carlin, G., et al., "Effect of anti-inflammatory drugs on xanthine oxidase and xanthine oxidase induced depolymerization of hyaluronic acid," 16 (5):377-384 (1985).

Carruthers et al. "The science and art of dermal fillers for soft-tissue augmentation," J. Drugs Dermatol. 8(4):335-350 (2009).

Champion, et al., "Role of Target Geometry in Phagocytosis", S. Proc. Nat. Acad. Sci., Mar. 2008, 2006, vol. 103, No. 13, pp. 4930-4934.

Chin, Thomas M., et al., "Allergic Hypersensitivity to Lidocaine Hydrochloride", International journal of Dermatology, vol. 19, Apr. 1980, pp. 147-148.

Chvapil, "Collagen Sponae: Theory and Practice fo Medical Applications", J. Biomed Mater. Res., II, 721-741 (1977).

Clark et al., "The Influence of Triamcinolone Acetonide on Joint Stiffness in the Rat", J Bone Joint Surg Am, 1971; 53:1409-1414.

Cohen et al., "Organization and Adhesive Properties of the Hyaluronan Pericellular Coat of Chrondrocytes and Epithelial Cells", Biophys J., 2003; 85:1996-2005.

Cui et al; "The Comparison of Physicochemical Properties of Four Cross-Linked Sodium Hyaluronate Gels with Different Cross-Linking Agents"; Advanced Material Research; vols. 396-398; pp. 1506-1512; 2012.

Deland, "Intrathecal Toxicity Studies with Benzyl Alcohol", Toxicol Appl Pharmacol 1973; 25(2):153.

Desai et al., J Pharm Sci Feb. 1995; 84(2): 212-5.

Eyre et al., Top Curr. Chem., 2005, vol. 247, pp. 207-229.

Falcone et al. "Crosslinked hyaluronic acid dermal fillers: a comparison of rheological properties." J Biomed Mater Res A. 87(1):264-271 (2008).

Falcone et al, "Temporary polysaccharide dermal fillers: a model for persistance based on physical properties," Dermatol Surg. 35(8):1238-1243 (2009).

Farley, Jon S., et al., "Diluting Lidocaine and Mepivacaine in Balanced Salt Solution Reduces the Pain of Intradermal Injection", Regional Anesthesia 19(1):48-51, 1994.

(56) References Cited

OTHER PUBLICATIONS

Frati, Elena et al., "Degradation of hyaluronic acid by photosensitized riboflavin in vitro, Modulation of the effect of transition metals, radical quenchers, and metal chelators," Free Radical Biology Medicine 22 (7):1139-1144 (1997).
Fujinaga, Masahiko, et al., "Reproductive and Teratogenic Effects of Lidocaine in Sprague-Dawley Rats", Anesthesiology 65:626-632, 1986.
Gammaitoni, Arnold R., et al., "Pharmacokinetics and safety of continuously applied lidocaine patches 5%", Am J Health Syst Pharm, vol. 59, Nov. 15, 2002, pp. 2215-2220.
GinShiCel MH Hydroxy Propyl methyl Cellulose, Web Page http://www.ginshicel.en/MHPC.html, Nov. 12, 2008.
Gold MH, "Use of Hyaluronic acid fillers for the treatment of the aging face." Clin Interventions Aging 2(3): 369-376 (2007).
Goldberg "Breakthoughs in US dermal fillers for facial soft-tissue augmentation." J Cosmet Laser Ther. 11(4):240-247 (2009).
Graefe, Hendrik, et al., "Sensitive and specific photometric determination of mannitol in human serum," Clin Chem Lab Med. 41 (8):1049-1055 (2003).
Grecomoro et al., "Intra-Articular Treatment with Sodium Hyaluronate in Gonarthosis" A Controlled Clinical Trial Versus Placebo, Pharmatherapeutics, 1987; 5(2):137-41.
Grillo et al., "Thermal Reconstitution of Collagen from Solution and the Response to Its Heterologous Implantation", JSR II, No. 1, pp. 69-82 (1962).
Hassan et al., Effects of Adjuvants to local anaesthetics on their duration, III. Experimental studies of hyaluronic acid. Abstract Pub Med [Acts Anesthesiol Scand. May 1985; 29(4):384-8].
Hayashibara, "AA2G"; Sep. 23, 2007; http://web.archive.org/web/20079230720l0/http://www.hayashibara-intl.com/cosmetics/aa2g.html.
Helliwell, "Use of an Objective Measure of Articular Stiffness to Record Changes in Finger Joints After Intra-Articular Injection of Corticosteroid", As Theum Dis, 1997; 56:7.
Hertzberger-Ten et al., "Intra-Articular Steroids in Panciarticular Juvenile Chronic Arthritis", Type I, Eur J Ped 1991; 150:170-172.
Hetherington, "Potential for Patient Harm From Intrathecal Administration of Preserved Solutions", Med J Aust, 2000, 173(3):p. 141.
Hurst, "Adhesive Arachnoiditis and Vascular Blockage Caused By Detergents and Other Chemical Irritants: an Experimental Study", J Path Bact, 1955; 70:167.
Intramed Mannitol 20% m/v Infusion, package insert, pp. 1-2 (2010) http://home.intekom.com/pharm/intramed/manit120.html.
Jones et al., "Intra-Articular Hyaluronic Acid Compared to Intra-Articular Triamcinolone Hexacetonide in Inflammatory Knee Osteoarthritis", Osteoarthritis Cartilage, 1995 De, p. 269-273
Kablik et al. "Comparative physical properties of hyaluronic acid dermal fillers." Dermatol. Surg. Suppl. 35(Suppl. 1): 302-312 (2009).
Klein, "Skin Filling Collagen and Other Injectables of the Skin", Dermatologic Clinics, Jul. 2001, vol. 19, No. 3, pp. 491-588, ix, XP00919589.
Kopp et al., The Short-Term Effect of Intra-Articular Injections of Sodium Hyaluronate and Corticosteroid on Temporomandibular Joint Pain and Dysfunction, J. Oral Maxillofac, 1985.
Kulicke et al., "Visco-Elastic Properties of Sodium Hyaluronate Solutions," American Institue of Physics (2008).
Labschke, "Biocompatibility of Microparticles into Soft Tissue Fillers", 23 Semin. Cutan. Med. Surg., 214 (2004).
Lamar et al., "Antifibrosis Effect of Novel Gels in Anterior Cillary Slerotomy *ACS)," ARVO 2002 abstract.
Levy, Jaime et al., "Lidocaine hypersensitivity after subconjuctival injection", Can J Ophthalmol 2006; 41:204-6.
Lindvall et al.; "Influence of Various Compounds on the Degradation of Hyaluronic Acid by a Myeloperoxidase System"; Chemcio-Biological Interactions; vol. 90; pp. 1-12; 1994.
Lupo, MP., "Hyaluronic acid fillers in facial rejuvenation." Semin. Cutan. Med. Surg. 25(3):122-126 (2006).

Mackley, et al., "Delayed-Type Hypersensitivity to Lidocaine", Arch Dermatol, vol. 139, Mar. 2003, pp. 343-346.
Mancinelli et al., "Intramuscular High-Dose Triamcinolone Acetonide in the Treatment of Severe Chronic Asthma", West J. Med, Nov. 1997: 167(5), 322-329.
Matsumoto, Alan H, et al., "Reducing the Discomfort of Lidocaine Administration through pH Buffering," Journal of Vascular and Interventional Radiology, Jan.-Feb. 1994, pp. 171-175.
McCarty et al., "Inflammatory Reaction After Intrasynovial Injection of Microcrystalline Adrenocorticosteroid Esters", Arthritis and Theuymantism, 7(4):359-367 (1964).
McCleland, Plastic Reconstructive Surgery, 100(6), Nov. 1997, pp. 1466-1474.
McPherson, John M., "Development and Biochemical Characterization of Injectable Collagen," J. Dermatol Surg Oncol, 14(Suppll):Jul. 7, 1988, pp. 13-20.
Millay et al., "Vasoconstrictors in Facial Plastic Surgery"; Archives of Otolaryngology—Head & Neck Surgery; vol. 117; pp. 160-163; Feb. 1991.
Orvisky, B., et al., "High-molecular-weight hyaluronen—a valuable tool in testing the antioxidative activity of amphiphilic drugs stobadine and vinpocetine," Pharm.Biomed.Anal. 16:419-424 (1997).
Osmitrol (generic name Mannitol),Official FDA Information, side effects and uses, pp. 1-10 (2010) http://www.drugs.com/pro/osmitrol.html.
Park et al., "Biological Characterization of EDC-crosslinked Collagen-Hyaluronic Acid Matrix in Dermal Tissue Restoration", Biomaterials 24 (2003) 1631-1641.
Park et al., "Characerization of Prous Collagen/Hyaluronic Acid Scaffold Modified by 1-ethyl-3-(3-dimethylaminopropyl)carbodiimide cross-linking", Biomaterials 23 (2002): 1205-1212.
Powell; "Stability of Lidocaine in Aqueous Solution: Effect of Temperature, pH, Buffer, and Metal Ions on Amide Hydrolysis"; Pharmaceutical Research; vol. 4, No. 1, 1987.
Prestwich, Glenn D., "Evaluating drug efficacy and toxicolgy in three dimensions: using synthetic extracelluar matrices in drug discovery," Accounts of Chemical Research 41 (1):139-148 (2008).
Rehakova, Milena, et al., "Properties of collagen and hyaluronic acid composite materials and their modifications by chemical crosslinking," Journal of Biomedical Research, vol. 30, 1996, pp. 36-372, XP002590342.
Remington's Pharmaceutical Science Mac Publishing Company, Easton, PA 16th Edition 1980.
Rosenblatt et al., "The Effect of Collagen Fiber Size Distribution on the Release Rate of Proteins from Collagen Matrices by Diffusion", J. Controlled Rel., 9, pp. 195-203 (1989).
Rosenblatt et al., "Chain Rigidity and Diffusional Release in Biopolymer Gels", Proceed. Inter. Symp. Control. Rel. Bioact. Mater., 20, pp. 264-265 (1993) Controlled Release Society, Inc.
Sannino et al., "Crosslinking of Cellulose Derivatives and Hyaluronic Acid with Water-Soluble Carbodiimide," Polymer 46 (2005)pp. 11206-11212.
SCULPTRA® Aesthetic (injectable poly-L-lactic acid) Directions for Use, Dermik Laboratories product insert (Jul. 2009), sanofi-aventis U.S. LLC.
Segura et al. "Crosslinked hyaluronic acid hydrogels: a strategy to functionalize and pattern." Biomaterials 26(4): 359-371 (2005).
Selvi et al, "Arthritis Induced by Corticosteroid Crystals", J. Rheumatology, 2004, 34:3.
Serban et al. "Modular Extracellular Matrices: Solutions for the Puzzle." Methods 45(1): 93-98 (2008).
Shu et al., "Synthesis and evaluation of injectable, in situ crosslinkable synthetic extracellular matrices for tissue engineering," J. Biomed. Mater. Res. A. 79(4): 902-912 (2006).
Silver et al., "Physical Properties of Hyaluronic Acid and Hydroxypropylmethylcellulose in Solution: Evaluation of Coating Ability," Journal of Applied Biomaterials, vol. 5, 89-98 (1994).
Skardal etal "Bioprinting Vessel-Like Constructs Using Hyaluronan Hydrogels Crosslinkedwith Tetrahedral Polyethylene Glyol Tetracrylates"; BioMaterials. Elsevier Science Publishers BV; vol. 31, No. 24; pp. 6173-6181; Aug. 1, 2010.

(56) References Cited

OTHER PUBLICATIONS

Smith, Kevin C., et al., "Five Percent Lidocaine Cream Applied Simultaneously to Skin and Mucose of the Lips Creates Excellent Anesthesia for Filler Injections", Dermatol Surg 2005; 31:1635-1637.
Tezel et al. "The science of hyaluronic acid dermal fillers," J. Cosmet. Laser Ther. 10(1): 35-42 (2008).
Visiol, Viscoelstic gel for use in ocular surgery, (2010) p.1, htt://www.trbchemedica.com/index.php/option=com_content&cas.
Waraszkiewicz, Sigmund M., et al., "Stability-Indicating High-Performance Liquid Chromatographic Analysis of Lidocaine Hydrochloride and Lidocaine Hydrochloride with Epinephrine Injectable Solutions", Journal of Pharmaceutical Sciences, vol. 70, No. 11, Nov. 1981, pp. 1215-1218.
Wahl, "European Evaluation of a New Hyaluronic Acid Filler Incorporating Lidocaine", Journal of Cosmetic Dermatology; vol. 7, pp. 298-303; 2008.
Weidmann; "New Hyaluronic Acid Filler for Subdermal and Long-Lasting Volume Restoration of the Face"; European Dermatology; pp. 65-68; 2009.
Xia, Yun et al., "Comparison of Effects of Lidocaine Hydrochloride, Buffered Lidocaine, Diphenhydramine, and Normal Saline After Intradermal Injection", Journal of Clinical Anesthesia 14:339-343, 2002.
Yeom et al. "Effect of Cross-Linking Reagents for Hyaluronic Acid Hydrogel Dermal Fillers on Tissue Augmentation and Regeneration." Bioconjugate Chem., 21(2):240-247 (2010).
Yui, Nobuhiko, et al., "Inflammation responsive degradation of crosslinked hyaluronic acid gels," Journal of Controlled release, 22 (1992) pp. 105-116.
Yui Nobuhiko, et al., "Photo-responsive degradation of heterogeneous hydrogels comprising crosslinked hyaluronic acid and lipid microspheres for temporal drug delivery," Journal of Controlled Release, 26 (1993) pp. 141-145.
Yun, YH et al. "Hyaluronan Microspheres for Sustained Gene Delivery and Site-Specific Targeting", Biomaterials, vol. 25, 2004, pp. 147-157.
Zheng et al. "In situ crosslinkable hyaluronan hydrogels for tissue engineering," Biomaterials 25(7-8): 1339-1348 (2004).
Zulian et al., Triamcinolone Acetonide and Hexacetonide Intra-Articular Treatment of Symmetrical Joints in Juvenile Idiopathic Arthritis: a Double-Blind Trial, Rheum 2004.
Helary et al., "Concentrated collagen hyrdogels as dermal substitutes", Biomaterials 31 (2010) 481-490.
Altman et al., "Adhesion, migration and mechanics of human adipose-tissue-derived stem cells on silk fibroin-chitosan matrix", Acts Biomaterials 8 (2010) 1388-1397.
Taguchi et al., "An improved method to prepare hyaluronic acid and type II collagen composits matrices", Journal of Biomedical Materials Research (2002), 61(2), 330-336.
Greco et al., "Hyaluronic Acid Stimulates Human Fibroblast Proliferation Within a Collagen Matrix", J. Cell. Physiol. 177 (3):465-473, 1996.
Calderon et al., "Type II Collagen-Hyaluronan Hydrogel—A Step Towards a Scaffold for Intervertebral Disc Tissue Engineering", European Cells and Materials, vol. 20, pp. 134-148, 2010.
Doillon et al., "Fibroblast growth on a porous collagen sponge containing hyaluronic acid and fibronectin", Biomaterials 8 (1987) 195-200.
Davidenko et al., "Collagen-hyaluronic acid scaffold for adipose tissue engineering", Acta Biomaterials 8 (2010) 3957-3988.
Crosslinking Technical Handbook, Thermo Scientific, pp. 1-18, published Apr. 2009.
Park et al., "In virelo evaluation of conjugated Hyaluronic acid with Ascorbic Acid", Journal of Bone & Joint Surgery, British vol. 92-B, XP-002708399, 2010.
Sterilization-microbiology, http://www.ask.com/wiki/Sterilization_(microbiology), pp. 1-9, Sep. 25, 2013.
Kreisel et al., "Cell-delivery therapeutics for adipose tissue regeneration", Advanced Drug Delivery Reviews 62 (2010) 796-813.
Tomihata, Kenji et al., Crosslinking of Hyaluronic Acid with Water-Soluable Carbodiimide, J. Biomed Mater Res., Feb. 1997, pp. 243-251, vol. 37(2).
Wang et al, Development of hyaluronic acid-based scaffolds for brain tissue engineering, Acta Biomaterials, 2009, 5, pp. 2371-2384.
Machine translation of JP 2002/080501 A, pp. 1-8, accessed Sep. 19, 2013.
Van Der Raat et al, Collagen family of proteins, FASEB J., 1991, 5, pp. 2814-2823.
Boule et al, Lip Augmentation and Contour Correction With a Ribose Cross-linked Collagen Dermal Filler, Journals of Drugs in Dermatology, 2009, 8, pp. 1-8.
Z-Hun Kim et al., A Composite Dermal Filler Comprising Cross-Linked Hyaluronic Acid and Human Collagen for Tissue Reconstrution, J. Microbiol. Biotechnol., 2015, pp. 399-406, 25 (3), The Korean Society for Microbiology & Biotechnology.
Ginshicel Mh, Hydroxy Propyl Methyl Cellulose, Retrieved on Nov. 12, 2008 http://www.ginshicel.cn/MHPC.html, 2007, p. 1-3, 2 (3).
Jones, et al., "Intra-articular hyaluronic acid compared to intra-articular triamcinolone hexacetonide in inflammatory knee osteoarthritis," Osteoarthritis and Cartilage, 1995, 269-273, 3.
Etienne et al, "Soft Tissue Augmentation Using Silk Gels: An in Vitro and in Vivo Study," J. Periodontol, 2009, 80, pp. 1852-1858.
Mast et al, "Hyaluronic acid degradation products induce neovascularization and fibroplasia in fetal rabbit wounds," Wound Repair and Regeneration, 1995, 3, pp. 66-72.
McCleland, et al., "Evaluation of Artecoll Polymethylmethacrylate Implant for Soft-Tissue Augmentation: Biocompatibility and Chemical Characterization," Plastic & Reconstructive Surgery, 1997, 1466-1474, 100 (6).
McPherson, et al., "Development and Biochemical Characterization of Injectable Collagen," Journal of Dermatol Surg Oncol, 1988, 13-20, 14 (Suppl 1) 7.
Millay, et al., "Vasoconstrictors in Facial Plastic Surgery," Arch Otolaryngol Head Neck Surg., 1991, 160-163, 117.
Vialle-Presles et al, "Immunohistochemical study of the biological fate of a subcutaneous bovine collagen implant in rat," Histochemistry, 1989, 91, pp. 177-184.
Visiol, TRB Chemedica Ophthalmic Line, Product Info, May 2014, p. 1-2, Geneva, CH.
Coleman et al., "Fat Grafting to the Breast Revisited: Safety and Efficacy," Plast. Reconstr. Surg., 2007, 119, pp. 775-785.
Samani et al., "Elastic moduli of normal and pathological human breast tissues: an inversion-technique based investigation of 169 samples," Phys. Med. Biol., 2007, 52, pp. 1565-1576.

HYALURONIC ACID-COLLAGEN MATRICES FOR DERMAL FILLING AND VOLUMIZING APPLICATIONS

This application is a continuation of U.S. patent application Ser. No. 15/609,967 filed May 31, 2017, now U.S. Pat. No. 9,795,711, which is a continuation of U.S. patent application Ser. No. 14/962,897 filed on Dec. 8, 2015, now U.S. Pat. No. 9,821,086, which is a divisional of U.S. patent application Ser. No. 13/667,581 filed on Nov. 2, 2012, now abandoned, which claims priority to U.S. Provisional Patent Application No. 61/555,970, filed Nov. 4, 2011, and also, which is a continuation-in-part of U.S. patent application Ser. No. 13/605,565, filed on Sep. 6, 2012, now abandoned, which claims priority to U.S. Provisional Patent Application No. 61/531,533, filed on Sep. 6, 2011, and which is a continuation-in-part of U.S. patent application Ser. No. 13/603,213, filed Sep. 4, 2012, now abandoned, which claims priority to U.S. Provisional Patent Application No. 61/531,533, filed Sep. 6, 2011, the entire disclosure of each of these applications being incorporated herein by this specific reference.

This application generally relates to biocompatible, implantable compositions and more specifically relates to hyaluronic acid-collagen based compositions useful as dermal fillers.

SUMMARY

The present invention generally relates to a soft tissue aesthetic product. In one aspect, the product comprises a filler comprising a hydrogel having a form suitable for injecting into human tissue; and a label comprising instructions to inject the filler into the human tissue; wherein the hydrogel comprises water, and a crosslinked macromolecular matrix described herein.

Some embodiments include a method of improving an aesthetic quality of soft tissue of a human being comprising: injecting a hydrogel composition into a soft tissue of the human being to thereby improve the aesthetic quality of the soft tissue; wherein the hydrogel composition comprises water, and a crosslinked macromolecular matrix described herein.

Some embodiments include a method of generating tissue comprising contacting a tissue with a hydrogel composition to generate an additional amount of the tissue, wherein the hydrogel composition comprises water and a crosslinked macromolecular matrix described herein.

Some crosslinked molecular matrices may comprise a hyaluronic acid component; and a collagen component; wherein the hyaluronic acid component is crosslinked to the collagen component by a crosslinking component; and wherein the crosslinking component comprises a plurality of crosslink units, wherein at least a portion of the crosslink units comprise an ester bond or an amide bond.

BRIEF DESCRIPTION OF THE DRAWINGS

Some aspects of the present disclosure may be more clearly understood with reference to the appended drawings of which.

DETAILED DESCRIPTION

Figure 1A:
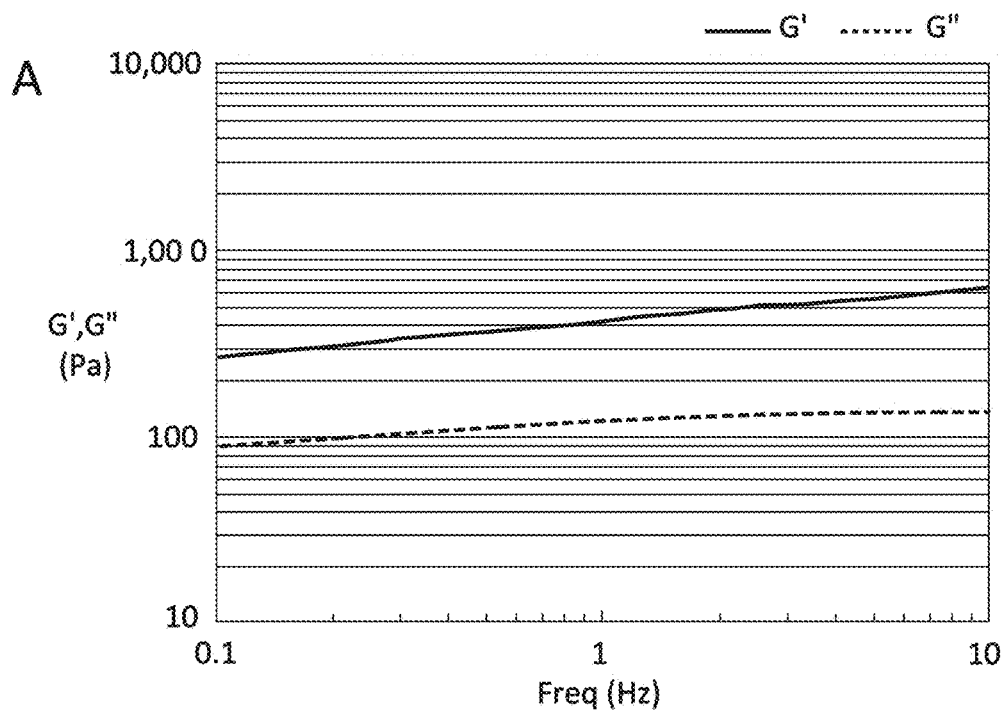
FIG. 1A is a plot of frequency sweep and FIG. 1B is a plot of strain sweep for a hydrogel in accordance with this disclosure.

Some embodiments include a method of improving an aesthetic quality of soft tissue of a human. Such a method may comprise injecting a hydrogel composition, or a composition comprising a hydrogel, into a soft tissue of the human being to thereby improve the aesthetic quality of the soft tissue.

Some embodiments may include a soft tissue aesthetic product comprising: a filler comprising a hydrogel having a form suitable for injecting into human tissue and a label comprising instructions to inject the filler into the human tissue.

A filler comprising a hydrogel or a hydrogel composition may be any kind of filler that is suitable for injecting into human tissue to improve an aesthetic quality of a soft tissue, such as a dermal filler, a breast augmentation or reconstruction filler, a lip filler, hand rejuvenation, or the like. When injected, a hydrogel may stimulate tissue in-growth and generation after being injected into the soft tissue. In some embodiments, a hydrogel may stimulate collagenesis after being injected into the soft tissue.

Injecting a hydrogel comprising a crosslinked macromolecular matrix comprising a hyaluronic acid component that is crosslinked to a collagen component may provide improved aesthetic quality for an extended duration, as compared to injecting an identical hydrogel except that hyaluronic acid component and the collagen component are not crosslinked.

Some embodiments include a method of generating tissue comprising contacting a tissue with a hydrogel composition to generate an additional amount of the tissue. This method may be used to generate tissue both ex vivo and in vivo. In some embodiments, contact between a tissue and a hydrogel may be ex vivo. In some embodiments, contact between a tissue and a hydrogel may be in vivo. Tissue types that may be generated include, but are not limited to, adipose tissue, muscle tissue, tendon tissue, cardiovascular tissue, neural tissue, bone tissue, and the like.

Some embodiments include a packaged product comprising a syringe loaded with a hydrogel and a needle. A syringe may be fitted with a needle of any size that is appropriate for injecting the hydrogel into the soft tissue of interest, such as a needle with about a #25, about a #30, or a larger gauge.

A filler comprising a hydrogel may be suitable for injection if it can be injected into the soft tissue of interest without unreasonable difficulty, and includes fillers that can be dispensed from cannulas having gauge as low as about #30 or about #25 under normal manual pressure with a smooth extrusion plateau.

Injection of a hydrogel may provide a soft tissue augmentation that mimics the natural components of the skin. A hydrogel may be injected intradermally or subcutaneously to augment soft tissue and to repair or correct congenital anomalies, acquired defects, or cosmetic defects. Examples of such conditions include congenital anomalies such as hemifacial microsomia, malar and zygomatic hypoplasia, unilateral mammary hypoplasia, pectus excavatum, pectoralis agenesis (Poland's anomaly), and velopharyngeal incompetence secondary to cleft palate repair or submucous cleft palate (as a retropharyngeal implant); acquired defects (post traumatic, post surgical, or post infectious) such as depressed scars, subcutaneous atrophy (e.g., secondary to discoid lupus erythematosus), keratotic lesions, enophthalmos in the enucleated eye (also superior sulcus syndrome), acne pitting of the face, linear scleroderma with subcutaneous atrophy, saddle-nose deformity, Romberg's disease, and unilateral vocal cord paralysis; and cosmetic defects such as glabellar frown lines, deep nasolabial creases, circum-oral geographical wrinkles, sunken cheeks, and mammary hypoplasia.

Crosslinked hyaluronic acid, collagen, and crosslinked collagen, such as those used in dermal fillers, do not promote cellular infiltration and tissue in-growth. Similarly, collagen simply blended into hyaluronic acid hydrogels does not promote tissue integration or de novo tissue generation. However, some hydrogels described herein do promote cellular migration into the hydrogels and tissue formation within the gels when implanted in vivo.

A hydrogel may comprise water and a crosslinked macromolecular matrix. Typically, a crosslinked molecular matrix may comprise a hyaluronic acid component and a collagen component, wherein the hyaluronic acid component is crosslinked to the collagen component by a crosslinking component. A crosslinking component may comprise a plurality of crosslink units, wherein at least a portion of the crosslink units comprise an ester bond or an amide bond.

A crosslinked macromolecular matrix for a hydrogel may be synthesized by coupling a hyaluronic acid with a collagen using a coupling agent, such as a carbodiimide. In these hydrogels, hyaluronic acid may serve as a biocompatible water-binding component, providing bulk and isovolumetric degradation. Additionally, collagen may impart cell adhesion and signaling domains to promote cell attachment, migration, and other cell functions such as extra-cellular matrix deposition. The biopolymers form homogeneous hydrogels with tunable composition, swelling, and mechanical properties. Compositions can be made to be injectable for minimally invasive implantation through syringe and needle.

Hyaluronic acid is a non-sulfated glycosaminoglycan that enhances water retention and resists hydrostatic stresses. It is non-immunogenic and can be chemically modified in numerous fashions. Hyaluronic acid may be anionic at pH ranges around or above the pKa of its carboxylic acid groups.

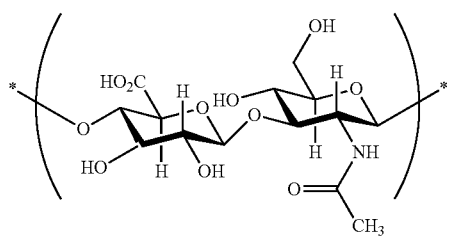

Hyaluronic Acid

Collagen is a protein that forms fibrils and sheets that bear tensile loads. Collagen also has specific integrin-binding sites for cell adhesion and is known to promote cell attachment, migration, and proliferation. Collagen may be positively charged because of its high content of basic amino acid residues such as arginine, lysine, and hydroxylysine.

Because hyaluronic acid may be anionic and collagen may be cationic, the two macromolecules may form polyionic complexes in aqueous solution. A polyionic complex may be significantly less soluble in water than either hyaluronic acid or collagen, and thus may precipitate out of aqueous solution when the two macromolecules are together in a mixture.

Under certain conditions, a hyaluronic acid and a collagen may be combined in an aqueous liquid in which both components are soluble. A hyaluronic acid and a collagen may then be crosslinked while both are dissolved in an aqueous solution to form a hydrogel. Reaction conditions such as the concentration of hyaluronic acid, the concentration of collagen, the pH of the solution, and salt concentration may be adjusted to help to prevent polyionic complex formation between anionic hyaluronic acid and cationic collagen. They may also help to prevent collagen microfibril formation.

Some embodiments include a method of crosslinking hyaluronic acid and collagen. This method generally comprises a dissolution step which results in an aqueous pre-reaction solution. In a dissolution step, hyaluronic acid and collagen are dissolved in an aqueous solution that has a low pH and/or a salt to form an aqueous pre-reaction solution.

A hyaluronic acid-collagen crosslinking method further comprises an activation step. In an activation step, an aqueous pre-reaction solution is modified at least by adding a water soluble coupling agent and/or by increasing the pH of the solution. If needed, a salt may also be added to keep the hyaluronic acid and collagen in solution at the higher pH. Thus, a crosslinking reaction mixture comprises hyaluronic acid and collagen dissolved or dispersed in an aqueous medium, a water soluble coupling agent, and a salt, and has a higher pH than the aqueous pre-reaction solution from which it was derived. The crosslinking reaction mixture is allowed to react to thereby crosslink the hyaluronic acid and the collagen.

In some embodiments, the pH of the aqueous pre-reaction solution may be increased and a substantial amount of fiber formation may be allowed to occur in the solution before adding the water soluble coupling agent. In some embodiments, the water soluble coupling agent may be added to the aqueous pre-reaction solution before substantially any fiber formation occurs.

A crosslinking reaction mixture can react to form a crosslinked macromolecular matrix. Since reaction occurs in an aqueous solution, a crosslinked macromolecular matrix may be dispersed in an aqueous liquid in hydrogel form as it is formed by a crosslinking reaction. A crosslinked macromolecular matrix may be kept in hydrogel form because, in many instances, a crosslinked macromolecular matrix may be used in hydrogel form.

In some embodiments, an aqueous pre-reaction solution or a crosslinking reaction mixture may further comprise about 10% to about 90% of an organic solvent in which hyaluronic acid has poor solubility, such as ethanol, methanol, isopropanol, or the like.

After a crosslinking reaction has occurred, the crosslinked macromolecular matrix may be particulated or homogenized through a mesh. This may help to form an injectable slurry or hydrogel. A mesh used for particulating a crosslinked macromolecular matrix may have any suitable pore size depending upon the size of particles desired. In some embodiments, the mesh may have a pore size of about 10 microns to about 100 microns, about 50 microns to about 70 microns, or about 60 microns.

A hydrogel comprising a crosslinked molecular matrix may be treated by dialysis for sterilization or other purposes. Dialysis may be carried out by placing a semipermeable membrane between the hydrogel and another liquid so as to allow the hydrogel and the liquid to exchange molecules or salts that can pass between the membrane.

A dialysis membrane may have a molecular weight cutoff that may vary. For example, the cutoff may be about 5,000 daltons to about 100,0000 daltons, about 10,000 daltons to about 30,000 daltons, or about 20,000 daltons.

The dialysis may be carried out against a buffer solution, or the liquid on the other side of the membrane from the hydrogel may be a buffer solution. In some embodiments, the buffer solution may be a sterile phosphate buffer solution that may comprise phosphate buffer, potassium chloride, and/or sodium chloride. A sterile phosphate buffer solution may be substantially isosmotic with respect to human physiological fluid. Thus, when dialysis is complete, the liquid component of a hydrogel may be substantially isosmotic with respect to human physiological fluid.

In some embodiments, a crosslinked macromolecular complex may further comprise an aqueous liquid. For example, the crosslinked macromolecular complex may absorb the aqueous liquid so that a hydrogel is formed. An aqueous liquid may comprise water with a salt dissolved in it, such as a phosphate buffer, sodium chloride, potassium chloride, etc. In some embodiments, an aqueous liquid may comprise water, sodium chloride at a concentration of about 100 mM to about 200 mM, potassium chloride at a concentration of about 2 mM to about 3 mM, and phosphate buffer at a concentration of about 5 mM to about 15 mM, wherein the pH of the liquid is about 7 to about 8.

A hydrogel may be used in a soft tissue aesthetic product. A soft tissue aesthetic product may comprise: an aesthetic device having a form suitable for injecting or implanting into human tissue; and a label comprising instructions to inject or implant the aesthetic component into human tissue; wherein the aesthetic device comprises a crosslinked macromolecular matrix described herein. Some products may comprise the crosslinked macromolecular matrix in hydrogel form.

Some embodiments include a method of improving an aesthetic quality of an anatomic feature of a human being comprising: injecting or implanting an aesthetic device into a tissue of the human being to thereby improve the aesthetic quality of the anatomic feature; wherein the aesthetic device comprises a crosslinked macromolecular matrix comprising described herein. In some embodiments, the crosslinked macromolecular matrix used in the product may be in hydrogel form.

In some embodiments, a hydrogel of a crosslinked macromolecular complex may have a storage modulus of about 1 Pa to about 10,000 Pa, about 50 Pa to 10,000 Pa, about 500 Pa to about 1000 Pa, about 556 Pa, about 560 Pa, about 850 Pa, about 852 Pa, or any value in a range bounded by, or between, any of these values.

In some embodiments, a hydrogel of a crosslinked macromolecular complex may have a loss modulus of about 1 Pa to about 500 Pa, about 10 Pa to 200 Pa, about 100 Pa to about 200 Pa, about 20 Pa, about 131 Pa, about 152 Pa, or any value in a range bounded by, or between, any of these values.

In some embodiments, a hydrogel of a crosslinked macromolecular complex may have an average extrusion force of about 20 N to 30 N, or about 25 N, when the hydrogel is forced through a 30 G needle syringe by moving the plunger of a 1 mL syringe containing the hydrogel at a rate of 100 mm/min for about 11 mm, and measuring the average force from about 4 mm to about 10 mm.

A crosslinked macromolecular complex may have tunable swelling properties based on reaction conditions and hydrogel dilution. In some embodiments, a crosslinked macromolecular complex may have a swelling ratio of about 1 to about 7. A swelling ratio is the ratio of the weight of the crosslinked macromolecular complex when saturated with water to the weight of the crosslinked macromolecular complex without any water. More specifically, the swelling ratio is the ratio of the mass of the gel which has been allowed to fully swell to the mass of the gel at its initial concentration.

In a crosslinking reaction, the molecular weight of a hyaluronic acid may vary. In some embodiments, a hyaluronic acid may have a molecular weight of about 500,000 daltons to about 10,000,000 daltons, about 1,000,000 daltons to about 5,000,000 daltons, or about 1,000,000 daltons to about 3,000,000 daltons. When the crosslinking reaction occurs, the resulting crosslinked macromolecular product may have a hyaluronic acid component derived from the hyaluronic acid in the crosslinking reaction. Thus, the ranges recited above may also apply to the molecular weight of a hyaluronic acid component, e.g. about 500,000 daltons to about 10,000,000 daltons, about 1,000,000 daltons to about 5,000,000 daltons, or about 1,000,000 daltons to about 3,000,000 daltons. The term "molecular weight" is applied in this situation to a portion of the matrix even though the hyaluronic acid component may not actually be a separate molecule due to the crosslinking.

The concentration of hyaluronic acid in an aqueous pre-reaction solution or a crosslinking reaction mixture may vary. In some embodiments, hyaluronic acid is present at about 3 mg/mL to about 100 mg/mL, about 6 mg/mL to about 24 mg/mL, about 1 mg/mL to about 30 mg/mL, about 1.7 mg/mL, about 3 mg/mL, about 6 mg/mL, about 12 mg/mL, about 16 mg/mL, or about 24 mg/mL.

Any type of collagen may be used in the methods and compositions described herein. In some embodiments, collagen type I, collagen type III, collagen type IV, collagen type VI, or a combination thereof, may be used. In some embodiments, a collagen or a collagen component comprises collagen type I or collagen type III. In some embodiments, the collagen component comprises collagen type V.

A collagen may be derived from cell culture, animal tissue, or recombinant means, and may be derived from human, porcine, or bovine sources. Some embodiments comprise collagen derived from human fibroblast culture. Some embodiments comprise collagen that has been denatured to gelatin. The source and/or collagen extraction/processing conditions can alter the way in which collagen macromolecules bundle together to form supramolecular structures. These higher order structures can have effects on the gel physical properties (stiffness, viscosity) and may also have an effect on the reactivity of the collagen to crosslinking reagents.

Collagen concentration in an aqueous pre-reaction solution or a crosslinking reaction mixture may vary. In some embodiments, collagen may be present at a concentration of about 1 mg/mL to about 40 mg/mL, about 1 mg/mL to about 15 mg/mL, about 3 mg/mL to about 12 mg/mL, about 1.7 mg/mL, about 3 mg/mL, about 6 mg/mL, about 8 mg/mL, or about 12 mg/mL. The collagen concentration has an effect on the physical properties of the gel (stiffness, viscosity). In general, higher collagen concentrations lead to a higher elastic modulus.

In some embodiments, the weight ratio of hyaluronic acid to collagen in a aqueous pre-reaction solution or a aqueous pre-reaction solution or a crosslinking reaction mixture (e.g. [wt hyaluronic acid]/[wt collagen]) may be about 0.5 to about 3, about 1 to about 3, about 1 to about 2, about 1, or about 2. When the crosslinking reaction occurs, the resulting crosslinked macromolecular product may have a collagen component derived from the collagen in the crosslinking reaction. Thus, the resulting crosslinked macromolecular matrix may have a weight ratio of hyaluronic acid component to collagen component that corresponds to the weight ratio in the crosslinking reaction, e.g. about 0.5 to about 3, about 1 to about 3, about 1 to about 2, about 1, or about 2.

In other embodiments of the invention, the compositions have an HA to collagen ratio of between about 0.5 to 1 and about 7 to 1.

A salt may help to screen the negative charges of hyaluronic acid from positive charges of collagen, and may thus prevent precipitation of a polyionic ion complex from solution. However, high concentrations of salt may reduce the solubility of some components in solution. Thus, in some embodiments, the salt concentration of an aqueous pre-reaction solution or a crosslinking reaction mixture may be high enough to screen the charges so that the polyionic ion complex is not formed, but also low enough so that the components of the mixture remain in solution. For example, the total salt concentration of some aqueous pre-reaction solutions or crosslinking reaction mixtures may be about 10 mM to about 1 M, for example, between about 5 mM to about 0.5 M, for example, between about 2 mM to about 0.2 M.

Some salts in an aqueous pre-reaction solution or a crosslinking reaction mixture may be non-coordinating buffers. Any non-coordinating buffer may be used that is capable of buffering the mixture and does not coordinate with metal atoms or ions in the collagen. In some embodiments, the buffer does not react with the crosslinking reagents (carbodiimide and additive). For example, acetate or phosphate buffers may not be used in these embodiments. Examples of suitable non-coordinating buffers may include, but are not limited to, 2-(N-morpholino)ethanesulfonic acid (MES), 3-(N-morpholino)propanesulfonic acid (MOPS), 4-(2-hydroxyethyl)-1-piperazinyl)ethanesulfonic acid (HEPES), 3-[4-(2-hydroxyethyl)-1-piperazinyl]propanesulfonic acid (HEPPS), N-cyclohexyl-2-aminoethanesulfonic acid (CHES), N-cyclohexyl-3-aminopropanesulfonic acid (CAPS), etc.

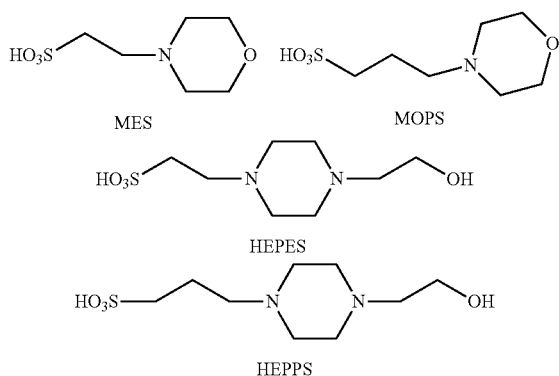

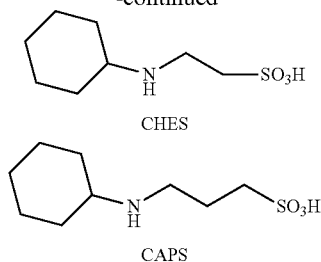

The concentration of a non-coordinating buffer may vary. For example, some aqueous pre-reaction solutions or crosslinking reaction mixtures may have a buffer concentration in a range of about 10 mM to about 1 M, about 10 mM to about 500 mM, about 20 mM to about 100 mM, or about 25 mM to about 250 mM. Some aqueous pre-reaction solutions or crosslinking reaction mixtures comprise MES at a concentration of about 20 mM to about 200 mM, about 20 mM to about 100 mM, about 100 mM, or about 180 mM.

Non-buffering salts may also be included in an aqueous pre-reaction solution or a crosslinking reaction mixture as an alternative to, or in addition, to buffering salts. Some examples may include sodium chloride, potassium chloride, potassium bromide, sodium bromide, lithium chloride, lithium bromide, sodium iodide, and potassium iodide. The concentration of a non-buffering salt may vary. For example, some mixtures may have a non-buffering salt concentration in a range of about 10 mM to about 1 mM, about 30 mM to about 500 mM, or about 50 mM to about 300 mM. In some embodiments, sodium chloride may be present at a concentration in a range of about 0.5% w/v to about 2% about 0.9% w/v, about 1.6% w/v, about 20 mM to about 1 mM, about 40 mM to about 500 mM, about 50 to 300 mM, about 80 mM to about 330 mM, about 150 mM, or about 270 mM.

The pH of an aqueous pre-reaction solution may be lower than the pH of a crosslinking reaction mixture. If the salt content of the aqueous pre-reaction solution is low, the pH may be lower to enhance solubility of the hyaluronic acid and the collagen. If the salt content is higher, the pH may be higher in the aqueous pre-reaction solution. In some embodiments, the pH of the aqueous pre-reaction solution is about 1 to about 8, about 3 to about 8, about 4 to about 6, about 4.7 to about 7.4, or about 5.4. For low salt concentrations, the pH may be about 1 to about 4 or about 1 to about 3.

In some embodiments, pH may be adjusted to neutral to allow collagen gelation or fiber formation before adding a coupling agent.

In some embodiments, the pH may be adjusted to neutral immediately prior to, around the time of, or after adding a coupling agent, such that collagen gelation is reduced or does not substantially occur.

Any water-soluble coupling agent may be used that can crosslink hyaluronic acid to collagen. Some non-limiting examples of a coupling agent include carbodiimides such as N,N'-dicyclohexylcarbodiimide (DCC), N,N'-diisopropylcarbodiimide (DIC), or 1-ethyl-3-(3-dimethylaminopropyl)carbodiimide (EDC). Carbodiimide coupling agents may facilitate ester or amide bond formation without becoming part of the linkage. However, other coupling agents that become part of the crosslinking group may be used. The concentration of a coupling agent may vary. In some embodiments, a coupling agent may be present at about 2 mM to about 150 mM, about 2 mM to about 50 mM, about 20 mM to about 100 mM, or about 50 mM. In some embodiments, the coupling agent is EDC that is present at a concentration of about 20 mM to about 100 mM, about 2 mM to about 50 mM, or about 50 mM.

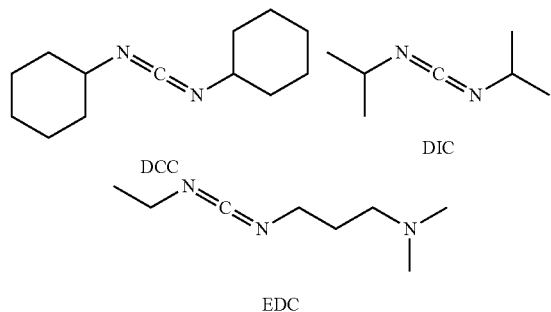

DCC

DIC

EDC

As a result of a crosslinking reaction, a crosslinked macromolecular matrix may comprise a crosslinking component that crosslinks or covalently connects the hyaluronic acid component to the collagen component. A crosslink component comprises a plurality of crosslink units, or individual covalent bonding links, between the hyaluronic acid component and the collagen component. At least a portion of the crosslink units comprise an ester bond or an amide bond. In some embodiments, at least a portion of the crosslink units may be —CON— or —CO$_2$—, where the N is a nitrogen from an amino acid residue.

An activating agent may be used to increase the ratio of amide bonds compared to ester bonds formed in the crosslinked product. In some embodiments, an activating agent may be a triazole such as hydroxybenzotriazole (HOBT) or 1-hydroxy-7-azabenzotriazole (HOAT); a fluorinated phenol such as pentafluorophenol; a succinimide such as N-hydroxysuccinimide (NHS) or N-hydroxysulfosuccinimide (sulfoNHS), and the like.

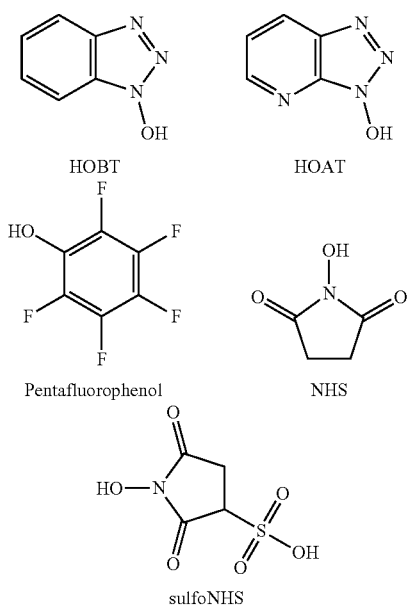

HOBT

HOAT

Pentafluorophenol

NHS sulfoNHS

The concentration of an activating agent may vary. In some embodiments, the activating agent may have a concentration of about 2 mM to about 200 mM, about 2 mM to about 50 mM, about 20 mM to about 100 mM, or about 50 mM. In some embodiments, the activating agent may be NHS or sulfoNHS is at a concentration of about 2 mM to about 50 mM. In some embodiments, the activating agent may be N-hydroxysulfosuccinimide, sodium salt, at a concentration of about 20 mM to about 100 mM, or about 50 Mm.

In some embodiments, a crosslinking reaction mixture may comprise a carbodiimide coupling agent and an activating agent. In some embodiments, the coupling agent is EDC and the activating agent is NHS or sulfoNHS. In some embodiments EDC is present at a concentration of about 2 mM to about 50 mM and NHS or sulfoNHS is present at about 2 mM to about 50 mM.

In some embodiments, a crosslinking reaction mixture may comprise hyaluronic acid at a concentration of about 1.7 mg/mL, collagen at a concentration of about 1.7 mg/mL, 2-(N-morpholino)ethanesulfonic acid at a concentration of about 100 mM, sodium chloride at a concentration of about 0.9 wt % or about 150 mM, 1-ethyl-3-(3-dimethylaminopropyl)carbodiimide at a concentration of about 50 mM, and N-hydroxysulfosuccinimide sodium salt at a concentration of about 50 Mm, wherein the solution has a pH of about 5.4.

In some embodiments, a crosslinking reaction mixture may comprise hyaluronic acid at a concentration of about 6 mg/mL, collagen at a concentration of about 6 mg/mL, 2-(N-morpholino)ethanesulfonic acid at a concentration of about 180 mM, sodium chloride at a concentration of about 1.6 wt % or about 270 mM, 1-ethyl-3-(3-dimethylaminopropyl)carbodiimide at a concentration of about 50 mM, and N-hydroxysulfosuccinimide sodium salt at a concentration of about 50 mM, wherein the solution has a pH of about 5.4.

In some embodiments, a crosslinking reaction mixture may comprise hyaluronic acid at a concentration of about 16 mg/mL of, collagen at a concentration of about 8 mg/mL, 2-(N-morpholino)ethanesulfonic acid at a concentration of about 100 mM, sodium chloride at a concentration of about 0.9 wt % or about 150 mM, 1-ethyl-3-(3-dimethylaminopropyl)carbodiimide at a concentration of about 50 mM, and N-hydroxysulfosuccinimide sodium salt at a concentration of about 50 mM, wherein the solution has a pH of between about 4.5 and 5.5, for example, about 5.2.

In some embodiments, a crosslinking reaction mixture may comprise hyaluronic acid at a concentration of about 12 mg/mL, collagen at a concentration of about 12 mg/mL, 2-(N-morpholino)ethanesulfonic acid at a concentration of about 100 mM, sodium chloride at a concentration of about 0.9 wt % or about 150 mM, 1-ethyl-3-(3-dimethylaminopropyl)carbodiimide at a concentration of about 50 mM, and N-hydroxysulfosuccinimide sodium salt at a concentration of about 50 mM.

In some embodiments, a crosslinking reaction mixture may comprise hyaluronic acid at a concentration of about 3 mg/mL, collagen at a concentration of about 3 mg/mL, 2-(N-morpholino)ethanesulfonic acid at a concentration of about 100 mM, sodium chloride at a concentration of about 0.9 wt % or about 150 mM, 1-ethyl-3-(3-dimethylaminopropyl)carbodiimide at a concentration of about 50 mM, and N-hydroxysulfosuccinimide sodium salt at a concentration of about 50 mM, wherein the solution has a pH of about 5.4.

In some embodiments, a crosslinking reaction mixture may comprise hyaluronic acid at a concentration of about 12 mg/mL, collagen at a concentration of about 6 mg/mL, 2-(N-morpholino)ethanesulfonic acid at a concentration of about 100 mM, sodium chloride at a concentration of about 0.9 wt % or about 150 mM, 1-ethyl-3-(3-dimethylaminopropyl)carbodiimide at a concentration of about 50 mM, and N-hydroxysulfosuccinimide sodium salt at a concentration of about 50 mM, wherein the solution has a pH of about 5.4.

In some embodiments, a crosslinking reaction mixture may comprise hyaluronic acid at a concentration of about 24 mg/mL, collagen at a concentration of about 12 mg/mL, 2-(N-morpholino)ethanesulfonic acid at a concentration of about 100 mM, sodium chloride at a concentration of about 0.9 wt % or about 150 mM, 1-ethyl-3-(3-dimethylaminopropyl)carbodiimide at a concentration of about 50 mM, and N-hydroxysulfosuccinimide sodium salt at a concentration of about 50 mM, wherein the solution has a pH of about 5.4.

In some embodiments, a crosslinking reaction mixture may comprise hyaluronic acid at a concentration of about 1 mg/mL to about 20 mg/mL, collagen at a concentration of about 1 mg/mL to about 15 mg/mL, 2-(N-morpholino)ethanesulfonic acid at a concentration of about 20 mM to about 200 mM, sodium chloride at a concentration of about 0.5 wt % to about 2 wt % or about 80 mM to about 330 mM, 1-ethyl-3-(3-dimethylaminopropyl)carbodiimide at a concentration of about 20 mM to about 100 mM, and N-hydroxysulfosuccinimide sodium salt at a concentration of about 20 mM to about 100 mM, wherein the solution has a pH of about 4 to about 6.

Example 1

Method of Making an Injectable Composition

Solutions of hyaluronic acid (HA) and collagen were produced by dissolving 15 mg of 2.0 MDa hyaluronic acid in 5 mL of human collagen(III) solution at 3 mg/mL in 0.01 N hydrochloric acid (Fibrogen). The hyaluronic acid/collagen solution was then lyophilized at −50° C. and 0.02 Torr. The resulting sponges were soaked in 20 mL of ethanol: water mixture at ratios varying from 1:2 to 5:1 with 50 mM of 1-ethyl-3-(3-dimethylaminopropyl) carbodiimide and 50 mM of N-hydroxysulfosuccinimide sodium salt for 24 hrs. The crosslinked gels were then washed in 70% isopropanol/30% water for sterilization followed by five washes in sterile phosphate buffer for purification.

Example 2

Method of Making an Injectable Composition

A solution of HA at 3.4 mg/mL was created by dissolving 34 mg of 2 MDa HA in 10 mL of 100 mM MES buffer with 0.9 wt % NaCl, pH 4.7. Upon full hydration and dissolution of the HA, this solution was mixed with 10 mL of 3.4 mg/mL human collagen(III) solution in 100 mM HCl. The pH of the resulting HA/collagen(III) solution was adjusted to 5.4 with 10 mM NaOH solution. EDC (192 mg) and 217 mg of sulfoNHS (50 mM each) were added to the HA/collagen(III) solution and mixed thoroughly. The crosslinking reaction proceeded for 18 hrs before the gel was particulated through a 100 micron pore-sized mesh.

Example 3

Method of Making an Injectable Composition

Rat tail collagen(I) in 0.01 N hydrochloric acid (Invitrogen) was concentrated from 5 mg/mL to 8 mg/mL using a centrifugal filtration device with 20 kDa molecular weight cutoff. HA (160 mg, 2 MDa) was added to 10 mL of the collagen solution and allowed to hydrate for 60 minutes. The solution was then homogenized by passing from syringe to syringe through a luer-luer connector. NaCl (93 mg) and 201 mg of MES were added to the solution and mixed. EDC (98 mg) and 111 mg of sulfoNHS were added to the solution and quickly mixed. Finally, 200 µL of 1 N NaOH was added to the solution which was mixed by syringe-to-syringe passing. The reaction solution was transferred to a glass vial and centrifuged for 5 min at 4000 RPM to remove air bubbles. The gel was then particulated through a 60 micron pore-sized mesh. Following sizing, the gel was sterilized by dialysis through a 20 kDa molecular-weight cut-off cellulose ester membrane against 70% isopropanol/30% water for 3 hrs at 4° C. Dialysis was then continued against sterile phosphate buffer for 48 hrs at 4° C. with three changes of buffer. The gel was then dispensed into syringes under aseptic conditions.

Example 4

Method of Making an Injectable Composition

Rat tail collagen(I) in 0.01 N hydrochloric acid (Invitrogen) was concentrated from 5 mg/mL to 12 mg/mL using a centrifugal filtration device with 20 kDa molecular weight cutoff. HA (120 mg, 2 MDa) was added to 10 mL of the collagen solution and allowed to hydrate for 60 minutes. The solution was then homogenized by passing from syringe to syringe through a luer-luer connector. NaCl (93 mg) and 201 mg of MES were added to the solution and mixed. EDC (98 mg) and 111 mg of sulfoNHS were added to the solution and quickly mixed. Finally, 200 µL of 1 N NaOH was added to the solution which was mixed by syringe-to-syringe passing. The reaction solution was transferred to a glass vial and centrifuged for 5 min at 4000 RPM to remove air bubbles. The gel was then particulated through a 60 micron pore-sized mesh. Following sizing, the gel was sterilized by dialysis through a 20 kDa molecular-weight cut-off cellulose ester membrane against 70% isopropanol/30% water for 3 hrs at 4° C. Dialysis was then continued against sterile phosphate buffer for 48 hrs at 4° C. with three changes of buffer. The gel was then dispensed into syringes under aseptic conditions.

Example 5

Method of Making an Injectable Composition

Rat tail collagen(I) in 0.01 N hydrochloric acid (Invitrogen) was concentrated from 5 mg/mL to 12 mg/mL using a centrifugal filtration device with 20 kDa molecular weight cutoff. HA (120 mg, 2 MDa) was added to 10 mL of the collagen solution and allowed to hydrate for 60 minutes. The solution was then homogenized by passing from syringe to syringe through a luer-luer connector. NaCl (93 mg), 201 mg of MES, and 200 µL of 1 N NaOH were added to the solution, mixed, and given 45 minutes for collagen polymerization. EDC (98 mg) and 111 mg of sulfoNHS were then added and the final solution was mixed by syringe-to-syringe passing. The reaction solution was transferred to a glass vial and centrifuged for 5 min at 4000 RPM to remove air bubbles. The gel was then particulated through a 60 micron pore-sized mesh. Following sizing, the gel was sterilized by dialysis through a 20 kDa molecular-weight cut-off cellulose ester membrane against 70% isopropanol/ 30% water for 3 hrs at 4° C. Dialysis was then continued against sterile phosphate buffer for 48 hrs at 4° C. with three changes of buffer. The gel was then dispensed into syringes under aseptic conditions.

Example 6

Rheology Characterization of the Compositions

Oscillatory parallel plate rheology was used to characterize the mechanical properties of gels using an Anton Paar MCR 301. A plate diameter of 25 mm was used at a gap height of 1 mm. A frequency sweep from 0.1 to 10 Hz at a fixed strain of 2% with logarithmic increase in frequency was applied followed by a strain sweep between 0.1% and 300% at a fixed frequency of 5 Hz with logarithmic increase in strain. The storage modulus (G') and loss modulus (G") were determined from frequency sweep measurements at 5 Hz.

Figure 1B:
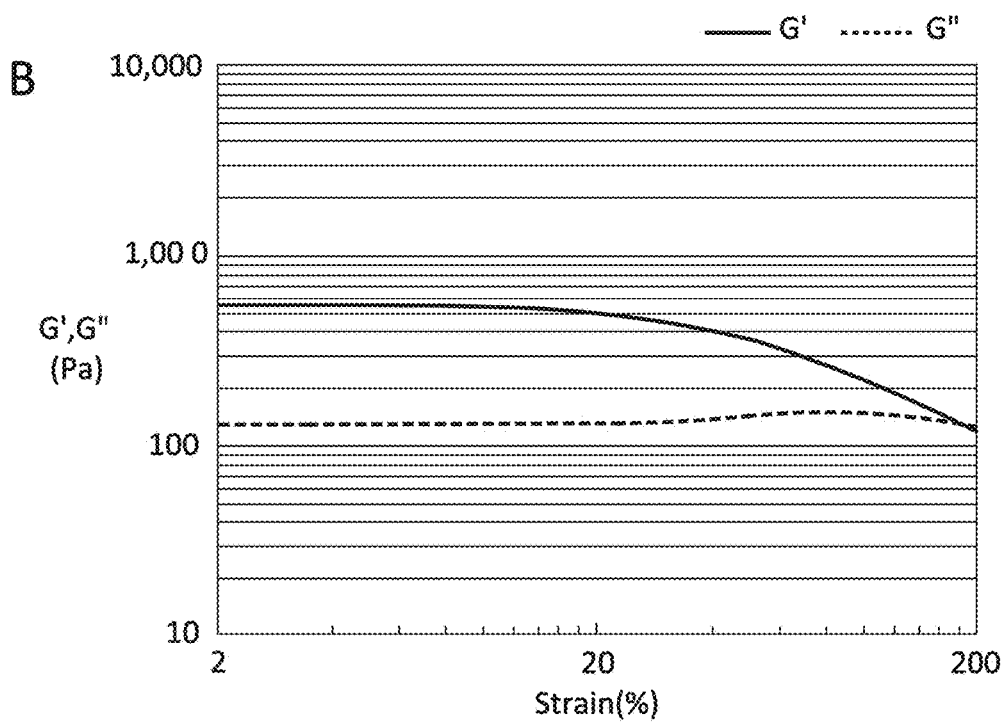

The gel from Example 4 had a storage modulus (G') of 556 Pa and loss modulus (G") of 131 Pa. The frequency sweep (A) and strain sweep (B) are shown in FIG. 1.

Example 7

Extrusion Test

In order to determine the force required to extrude the gels, they were ejected from 1 mL BD syringes through 30 G needles using an Instron 5564 with Bluehill 2 software. The plunger was pushed at a rate of 100 mm/min for 11.35 mm and the extrusion profile was recorded.

Figure 2:
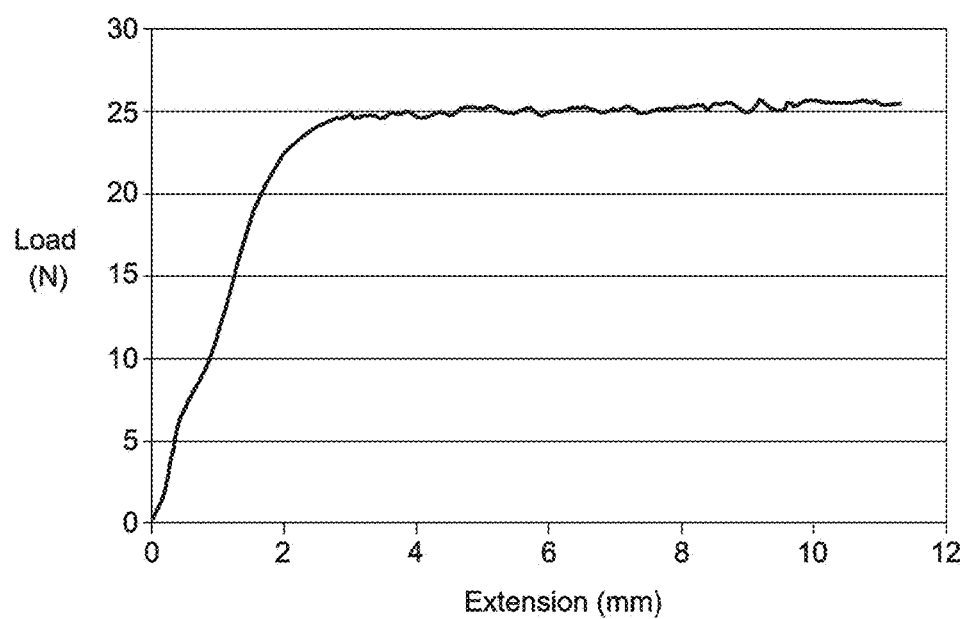
FIG. 2 is an extrusion profile through a 30 G needle for a hydrogel from Example 4.
Figure 3A:
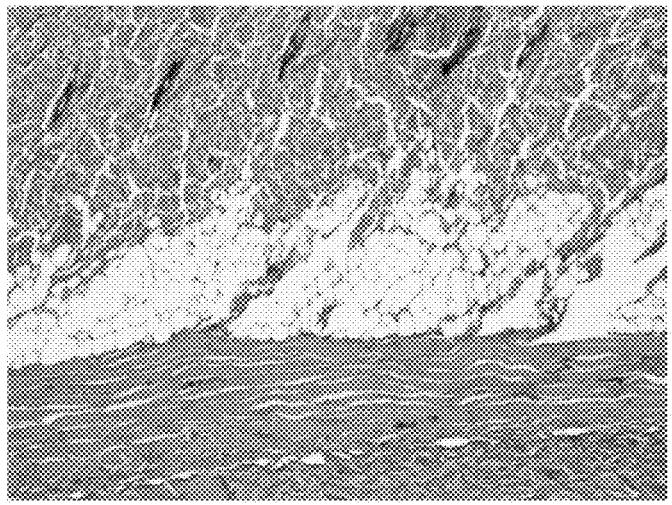
FIGS. 3A-3C shows respectively, micrographs (at 5×magnification) of (A) tissue adjacent to an implanted control composition of commercial crosslinked hyaluronic acid gel, (B) tissue adjacent to an implanted composition of Example 3, and (C) tissue adjacent to an implanted composition from Example 4.
Figure 3B:
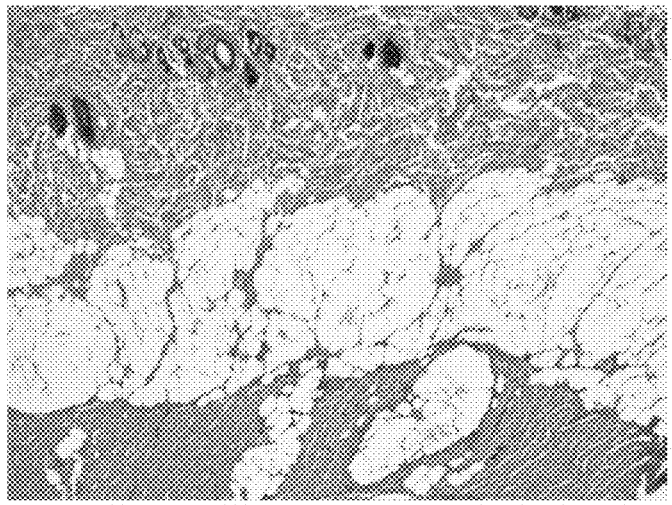
Figure 3C:
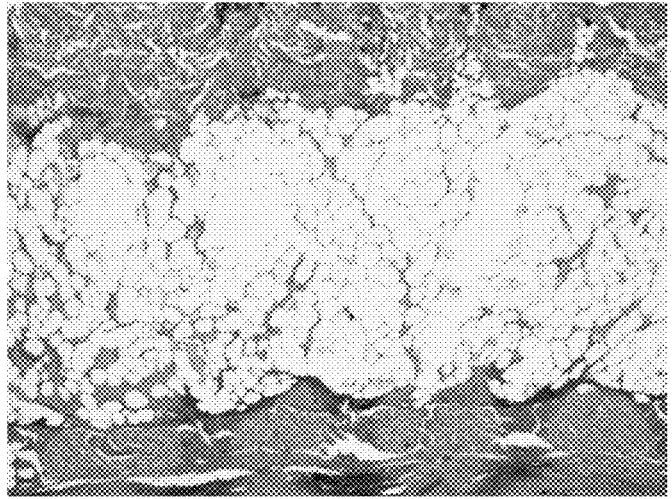

The extrusion profile through a 30 G needle for gel from Example 4 is shown in FIG. 2. The gel had an average extrusion force of 25 N from 4 through 10 mm.

Example 8

Method of Making Dermal Fillers

Hyaluronic acid, 2 MDa molecular weight, was dissolved in human collagen(I) solution in 0.01 N hydrochloric acid (Advanced BioMatrix). Sodium chloride was added at 0.9 wt % and 2-(N-morpholino)ethanesulfonic acid was added at 100 mM to the solution and mixed. The hyaluronic acid was allowed to hydrate for 1 hr and the solution was homogenized by syringe-to-syringe mixing. The pH of the solution was adjusted to 5.4 by addition of 1 N sodium hydroxide. 1-Ethyl-3-(3-dimethylaminopropyl) carbodiimide (50 mM) and N-hydroxysulfosuccinimide sodium salt (50 mM) were added to the hyaluronic acid/collagen solution and quickly mixed by syringe-to-syringe transfer. The solution was transferred to a glass vial and centrifuged for 5 min at 4000 RPM to remove air bubbles. The resulting gel was allowed to react for 16 hrs at 4° C. The gel was then particulated through a 100 micron pore-sized mesh. Following sizing, the gel was sterilized by dialysis through a 20 kDa molecular-weight cut-off cellulose ester membrane against 70% isopropanol/30% water for 3 hrs at 4° C. Dialysis was then continued against sterile phosphate buffer, pH 7.4, for 48 hrs at 4° C. with four changes of buffer. The gel was then dispensed into syringes under aseptic conditions.

This procedure was used to produce hydrogels with varying concentrations of hyaluronic acid and collagen. When required, human collagen(I) in 0.01 N hydrochloric acid was concentrated from 3 mg/mL to the desired reaction concentration in 20 kDa molecular-weight cut-off centrifugal filtration devices. A 50 mL sample of each gel was synthesized, sterilized by exposure to 70% isopropanol, and purified by dialysis against phosphate buffer, pH 7.4. The gels synthesized are described in Table 2 along with their rheological properties.

TABLE 2

Hyaluronic acid-human collagen(I) hydrogel synthesis concentrations and rheological properties

| Sample ID | [HA] (mg/mL) | [Col(I)] (mg/mL) | G' (Pa) | G" (Pa) |
|---|---|---|---|---|
| A | 3 | 3 | 199 | 24.6 |
| B | 12 | 6 | 1260 | 154 |
| C | 16 | 8 | 2450 | 288 |
| D | 12 | 12 | 3160 | 420 |
| E | 24 | 12 | 5440 | 433 |
| F | 12 | 3 | 1110 | 52.2 |
| G | 16 | 3 | 1490 | 60.6 |
| H | 20 | 3 | 1770 | 49.5 |

Example 9

Biopolymer Concentration of the Dermal Fillers

In order to determine the biopolymer concentration in gels, the weight of the hydrated gel was compared to that of dried gel. A 2 mL sample of gel was weighed and dried by flash-freezing in liquid nitrogen followed by lyophilization at −50° C. and 0.02 Torr. A solution of the appropriate buffer was also weighed and dried in the same fashion to account for salt content of the gel. The total solids content of the gel was calculated by dividing the dry weight by the wet volume, assuming 1 g/mL density for the wet gel, to give a value in mg/mL. The salt solids content was then subtracted from this value to determine the biopolymer concentration in the gel.

TABLE 3

Final concentrations of hyaluronic acid-human collagen(I) hydrogels

| Sample ID | [HA] (mg/mL) | [Col(I)] (mg/mL) | Final concentration (mg/mL) |
|---|---|---|---|
| A | 3 | 3 | 5.3 |
| B | 12 | 6 | 16.3 |
| C | 16 | 8 | 19.4 |
| D | 12 | 12 | 22.6 |
| E | 24 | 12 | 31.6 |

Example 10

Swelling Ratios

Swelling ratios relative to initial water content were determined for gels by increase in weight when equilibrated with phosphate buffer. For each gel, approximately 1 mL was injected into a 15 mL Falcon tube and weighed, followed by addition of 10 mL of phosphate buffered saline, pH 7.4. The gels were thoroughly mixed with the buffer and vortexed for 30 seconds. The gels were then allowed to equilibrate in the buffer for 48 hrs at 4° C. After this time, the suspensions were centrifuged at 4000 RPM in a swinging bucket rotor for 5 minutes. The supernatant buffer was then decanted and the weight of the swollen gel was measured. The swelling ratio was determined by dividing the final weight of the swollen gel by the weight of the initial gel.

TABLE 4

Swelling ratios of hyaluronic acid-human collagen(I) hydrogels

| Sample ID | [HA] (mg/mL) | [Col(I)] (mg/mL) | Swelling ratio |
|---|---|---|---|
| A | 3 | 3 | 0.96 |
| B | 12 | 6 | 1.67 |
| C | 16 | 8 | 1.69 |
| D | 12 | 12 | 1.49 |
| E | 24 | 12 | 1.65 |

Example 11

HA/Collagen for Facial Defects of Check

This example illustrates the use of compositions and methods disclosed herein for a facial disorder.

A 58-year-old woman presented with a lean face. She felt her face looked old, sad and bitter because of the less fullness of her cheek contour. Pre-operative evaluation of the person includes routine history and physical examination in addition to thorough informed consent disclosing all relevant risks and benefits of the procedure. The physician evaluating the individual determines that she is a candidate for administration of the dermal filler compositions and methods disclosed herein.

A composition of the invention, such as described in EXAMPLE 4, is provided in a 20 mL syringe. One-holed blunt infiltration cannulas (3 mm inner diameter) are used to place about 15 mL of the composition in the syringe subcutaneously and under superficial musculoaponeurotic system into the left and right cheeks.

The individual is monitored for approximately 7 days. The physician evaluates the treatment area and determines that the treatment was successful. The woman's cheeks are fuller than prior to treatment. Both the woman and her physician are satisfied with the results of the procedure because she looks younger than she did when she came in for treatment.

Example 12

Treatment of Facial Defects of Eyelids

This example illustrates the use of compositions and methods disclosed herein for a treatment of eyelid defects.

A 37-year-old woman presented with fine wrinkles around her eyes and she reports that her eyes made her look old and angry. Pre-operative evaluation of the person includes routine history and physical examination in addition to thorough informed consent disclosing all relevant risks and benefits of the procedure. The physician evaluating the individual determines that she is a candidate for administration of the dermal filler compositions and methods disclosed herein.

A composition, such as made as described in Example 5, is provided in a 20 mL syringe. About 2.5 mL of the composition is injected with a fine needle subcutaneously in the skin beneath the wrinkles into the regions adjacent the eyes.

The individual is monitored for approximately 7 days. The physician evaluates the eye of the patient and determines that the treatment was successful. Both the woman and her physician are satisfied with the results of the procedure because her eyes appear refreshed and the skin appears rejuvenated. Approximately one year after the procedure, the woman indicates that her quality of life has improved.

Example 13

Treatment of Acne Scars

This example illustrates the use of compositions and methods disclosed herein for treatment of acne scars.

A 25-year-old man presents with moderate acne scarring on his jaw line including depressions and pitting. He reports that he is dissatisfied with his appearance and feels he is socially inhibited due to his perception of his appearance. Pre-operative evaluation of the person includes routine history and physical examination in addition to thorough informed consent disclosing all relevant risks and benefits of the procedure. The physician evaluating the individual determines that he is a candidate for administration of the dermal filler compositions and methods disclosed herein.

A composition, such as that made as described in Example 12, is provided in 10 mL syringes. The physician injects a small amount of the composition below the skin in each depressed or pitted area of the patient's jawline to raise the area to match the surrounding skin.

The individual returns for a follow up visit with the physician in 14 days. The physician evaluates the patient and determines that the treatment was successful. The man reports he is satisfied with the results of the procedure because his skin is more smooth in appearance and the acne scarring is substantially less visible. Approximately six months after the procedure, the man returns for a follow up treatment. He reports to the physician that his quality of life has greatly improved since the procedure and he is no longer shy about his appearance.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

The terms "a," "an," "the," and similar referents used in the context of describing the invention (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of any claim. No language in the specification should be construed as indicating any non-claimed element essential to the practice of the invention.

Groupings of alternative elements or embodiments disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, the claims include all modifications and equivalents of the subject matter recited in the claims as permitted by applicable law. Moreover, any combination of the above-described elements in all possible variations thereof is contemplated unless otherwise indicated herein or otherwise clearly contradicted by context.

In closing, it is to be understood that the embodiments disclosed herein are illustrative of the principles of the claims. Other modifications that may be employed are within the scope of the claims. Thus, by way of example, but not of limitation, alternative embodiments may be utilized in accordance with the teachings herein. Accordingly, the claims are not limited to embodiments precisely as shown and described.

What is claimed is:

1. A soft tissue aesthetic product comprising:
   an injectable hydrogel composition comprising:
   (i) water; and
   (ii) a hyaluronic acid crosslinked with a collagen via a plurality of crosslink units, wherein at least a portion of the crosslink units comprise an amide bond; and wherein the hyaluronic acid concentration is from 6 mg/ml to 20 mg/ml; the collagen concentration is from 3 mg/ml to 12 mg/ml; the hyaluronic acid: collagen weight ratio is from 1:1 to 7:1; and the hydrogel has a storage modulus value of between 850 Pa and 5,000 Pa.

2. The product of claim 1, wherein the product further comprises a label, and wherein the label comprises instructions for injecting the hydrogel composition into a human tissue.

3. The product of claim 1, wherein the collagen is collagen type I, collagen type III, or a combination thereof.

4. The product of claim 3, wherein the collagen is collagen type I.

5. The product of claim 3, wherein the collagen is derived from a human or porcine source.

6. The product of claim 1, wherein the hyaluronic acid has a molecular weight of about 1,000,000 Da to about 5,000,000 Da.

7. The product of claim 1, wherein the hyaluronic acid has a molecular weight of about 1,000,000 Da to about 3,000,000 Da.

8. The product of claim 1, wherein the ratio of the hyaluronic acid to the collagen ranges from 1:1 to 2:1.

9. The product of claim 1, wherein the ratio of the hyaluronic acid to the collagen is 1:1.

10. The product of claim 1, wherein the hydrogel has a storage modulus value of between 1,000 Pa and 5,000 Pa.

11. The product of claim 1, wherein the hydrogel has a hyaluronic acid concentration of 12 mg/ml or 16 mg/ml.

12. The product of claim 1, wherein the hydrogel has a collagen concentration of 6 mg/ml, 8 mg/ml or 12 mg/ml.

13. The product of claim 1, wherein the hydrogel has a hyaluronic acid concentration of 12 mg/ml and a collagen concentration of 6 mg/ml.

14. The product of claim 1, wherein the hydrogel has a hyaluronic acid concentration of 12 mg/ml and a collagen concentration of 12 mg/ml.

15. The product of claim 1, wherein the hydrogel has a hyaluronic acid concentration of 16 mg/ml and a collagen concentration of 8 mg/ml.

16. The product of claim 2, wherein the injection is intradermal.

17. The product of claim 2, wherein the injection is subcutaneous.

18. The product of claim 2, wherein the human tissue contains adipose tissue.

* * * * *